US012702430B2

(12) United States Patent
Budyansky et al.

(10) Patent No.: US 12,702,430 B2
(45) Date of Patent: Aug. 11, 2026

(54) BONE HARVESTING

(71) Applicant: THE JOHNS HOPKINS UNIVERSITY, Baltimore, MD (US)

(72) Inventors: Maxim Budyansky, Baltimore, MD (US); Neil Shah, Baltimore, MD (US); Akhil Jay Khanna, Baltimore, MD (US); Khaled M. Kebaish, Baltimore, MD (US); Lee Hunter Riley, III, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 68 days.

(21) Appl. No.: 18/970,202

(22) Filed: Dec. 5, 2024

(65) Prior Publication Data

US 2025/0090179 A1 Mar. 20, 2025

Related U.S. Application Data

(63) Continuation of application No. 18/540,537, filed on Dec. 14, 2023, now Pat. No. 12,193,686, which is a (Continued)

(51) Int. Cl.
*A61B 17/16* (2006.01)
*A61B 17/3205* (2006.01)
(Continued)

(52) U.S. Cl.
CPC ...... *A61B 17/1635* (2013.01); *A61B 17/1642* (2013.01); *A61B 17/32053* (2013.01); (Continued)

(58) Field of Classification Search
CPC ............ A61B 17/1635; A61B 17/1642; A61B 17/32053; A61B 17/3472; A61M 1/76
See application file for complete search history.

(56) References Cited

U.S. PATENT DOCUMENTS 1,749,919 A 3/1930 Mierley
5,556,399 A 9/1996 Huebner
(Continued)

FOREIGN PATENT DOCUMENTS

AU 2013257164 12/2014
BR 112014027054 B1 5/2022
(Continued)

OTHER PUBLICATIONS

"U.S. Appl. No. 14/523,252, Advisory Action mailed Jan. 13, 2017", 4 pgs.
(Continued)

*Primary Examiner* — Si Ming Ku
(74) *Attorney, Agent, or Firm* — SCHWEGMAN LUNDBERG & WOESSNER, P.A.

(57) ABSTRACT

Methods and devices for harvesting cancellous bone are disclosed. The bone-harvesting device may include a cannula and a bone receptacle in communication with the cannula, wherein the cannula including a cutting surface positioned at or adjacent the distal end, the cutting surface being oriented at an angle, the angle being greater than 90 degrees relative to the longitudinal axis of the cannula, and the harvested bone is adapted to move from a position adjacent to the cutting surface through the cannula into the bone receptacle. The cutting surface of the cannula may be positioned at or adjacent the distal end, and positioned at least in part radially outward of the outer face of the cannula. The cannula may include a cutting surface positioned at or adjacent the distal end and an occluding geometry that partially occludes the distal end of the cannula adjacent the cutting surface. In addition, a suction port may be provided in communication with the bone receptacle.

20 Claims, 36 Drawing Sheets

Related U.S. Application Data continuation of application No. 17/173,050, filed on Feb. 10, 2021, now abandoned, which is a continuation of application No. 15/804,293, filed on Nov. 6, 2017, now abandoned, which is a continuation of application No. 14/523,252, filed on Oct. 24, 2014, now Pat. No. 9,833,248, which is a continuation of application No. PCT/US2013/032531, filed on Mar. 15, 2013.

(60) Provisional application No. 61/643,662, filed on May 7, 2012, provisional application No. 61/640,313, filed on Apr. 30, 2012.

(51) Int. Cl.

| | |
|---|---|
| ***A61B 17/34*** | (2006.01) |
| ***A61F 2/46*** | (2006.01) |
| ***A61M 1/00*** | (2006.01) |
| *A61B 17/00* | (2006.01) |
| *A61B 17/32* | (2006.01) |
| *A61B 17/3207* | (2006.01) |

(52) U.S. Cl.

CPC ........ *A61B 17/3472* (2013.01); *A61F 2/4644* (2013.01); *A61M 1/76* (2021.05); *A61B 2017/003* (2013.01); *A61B 2017/00477* (2013.01); *A61B 2017/00969* (2013.01); *A61B 17/1631* (2013.01); *A61B 17/1633* (2013.01); *A61B 2017/320008* (2013.01); *A61B 2017/320064* (2013.01); *A61B 17/320708* (2013.01); *A61B 2217/005* (2013.01); *A61F 2002/4649* (2013.01); *A61M 2210/02* (2013.01)

(56) References Cited

U.S. PATENT DOCUMENTS

| | | | | |
|---|---|---|---|---|
| 5,628,760 | A | 5/1997 | Knoepfler | |
| 5,833,628 | A | 11/1998 | Yuan et al. | |
| 5,885,301 | A | 3/1999 | Young | |
| 6,001,118 | A | 12/1999 | Daniel et al. | |
| 6,017,348 | A | 1/2000 | Hart et al. | |
| 6,022,354 | A | 2/2000 | Mercuri et al. | |
| 6,030,400 | A | 2/2000 | Johnson | |
| 6,110,177 | A | 8/2000 | Ebner et al. | |
| 6,554,803 | B1 * | 4/2003 | Ashman | B01L 3/0275 604/218 |
| 6,663,650 | B2 | 12/2003 | Sepetka et al. | |
| 6,755,837 | B2 | 6/2004 | Ebner | |
| 6,783,532 | B2 | 8/2004 | Steiner et al. | |
| 6,824,545 | B2 | 11/2004 | Sepetka et al. | |
| 7,077,846 | B2 | 7/2006 | Parmigiani | |
| 7,462,181 | B2 | 12/2008 | Kraft et al. | |
| 7,637,872 | B1 * | 12/2009 | Fox | A61B 10/025 600/36 |
| 7,762,181 | B2 | 7/2010 | Boland et al. | |
| 8,100,935 | B2 | 1/2012 | Rosenbluth et al. | |
| 8,252,017 | B2 | 8/2012 | Paul, Jr. et al. | |
| 8,425,546 | B2 | 4/2013 | Perez-cruet et al. | |
| 8,795,305 | B2 | 8/2014 | Martin et al. | |
| 8,864,687 | B2 | 10/2014 | May et al. | |
| 9,833,248 | B2 | 12/2017 | Budyansky et al. | |
| 9,833,252 | B2 | 12/2017 | Sepetka et al. | |
| 9,883,248 | B2 | 1/2018 | Kitazato et al. | |
| 12,193,686 | B2 | 1/2025 | Budyansky et al. | |
| 2003/0078586 | A1 | 4/2003 | Shapira | |
| 2004/0153005 | A1 | 8/2004 | Krueger | |
| 2005/0216050 | A1 | 9/2005 | Sepetka et al. | |
| 2006/0056270 | A1 | 3/2006 | Lee | |
| 2007/0016100 | A1 | 1/2007 | Miller | |
| 2007/0038227 | A1 | 2/2007 | Massicotte et al. | |
| 2007/0055282 | A1 | 3/2007 | Muschler | |
| 2007/0276352 | A1 | 11/2007 | Crocker et al. | |
| 2007/0293788 | A1 | 12/2007 | Entrekin et al. | |
| 2008/0045857 | A1 | 2/2008 | Miller et al. | |
| 2008/0119759 | A1 | 5/2008 | Mclain | |
| 2008/0139961 | A1 | 6/2008 | Slama et al. | |
| 2008/0243029 | A1 | 10/2008 | Howard et al. | |
| 2009/0187116 | A1 | 7/2009 | Noishiki et al. | |
| 2009/0306630 | A1 | 12/2009 | Locke et al. | |
| 2010/0094269 | A1 | 4/2010 | Pellegrino et al. | |
| 2010/0185117 | A1 | 7/2010 | Lyon | |
| 2010/0298835 | A1 | 11/2010 | Ralph et al. | |
| 2011/0213336 | A1 | 9/2011 | Cucin | |
| 2012/0310251 | A1 | 12/2012 | Sepetka et al. | |
| 2014/0276403 | A1 | 9/2014 | Follmer et al. | |
| 2015/0045799 | A1 | 2/2015 | Budyansky et al. | |
| 2018/0070963 | A1 | 3/2018 | Budyansky et al. | |
| 2021/0186526 | A1 | 6/2021 | Budyansky et al. | |
| 2024/0115273 | A1 | 4/2024 | Budyansky et al. | |

FOREIGN PATENT DOCUMENTS

| | | | |
|---|---|---|---|
| CN | 104379073 | A | 2/2015 |
| EP | 1867292 | A1 | 12/2007 |
| IN | 413163 | | 11/2022 |
| JP | 2005118295 | A | 5/2005 |
| RU | 2223056 | C2 | 2/2004 |
| RU | 65382 | U1 | 8/2007 |
| RU | 2336030 | C1 | 10/2008 |
| WO | WO-03073945 | A1 | 9/2003 |
| WO | WO-2007057928 | A1 | 5/2007 |
| WO | WO-2009086482 | A1 | 7/2009 |
| WO | WO-2009149250 | A1 | 12/2009 |
| WO | WO-2012037552 | A2 | 3/2012 |
| WO | WO-2013165616 | A1 | 11/2013 |
| WO | WO-2013165616 | A8 | 11/2014 |

OTHER PUBLICATIONS

"U.S. Appl. No. 14/523,252, Advisory Action mailed Aug. 12, 2015", 3 pgs.

"U.S. Appl. No. 14/523,252, Examiner Interview Summary mailed Aug. 5, 2015", 3 pgs.

"U.S. Appl. No. 14/523,252, Examiner Interview Summary mailed Dec. 21, 2016", 3 pgs.

"U.S. Appl. No. 14/523,252, Final Office Action mailed Jun. 25, 2015", 18 pgs.

"U.S. Appl. No. 14/523,252, Final Office Action mailed Oct. 6, 2016", 20 pgs.

"U.S. Appl. No. 14/523,252, Non Final Office Action mailed Jan. 30, 2015", 16 pgs.

"U.S. Appl. No. 14/523,252, Non Final Office Action mailed May 11, 2016", 18 pgs.

"U.S. Appl. No. 14/523,252, Notice of Allowance mailed Aug. 7, 2017", 8 pgs.

"U.S. Appl. No. 14/523,252, Response filed Jan. 7, 2015 to Restriction Requirement mailed Dec. 24, 2014", 3 pgs.

"U.S. Appl. No. 14/523,252, Response filed Mar. 6, 2017 to Advisory Action mailed Jan. 13, 2017", 21 pgs.

"U.S. Appl. No. 14/523,252, Response filed Mar. 31, 2015 to Non Final Office Action mailed Jan. 30, 2015", 13 pgs.

"U.S. Appl. No. 14/523,252, Response filed Aug. 4, 2015 to Final Office Action mailed Jun. 25, 2015", 11 pgs.

"U.S. Appl. No. 14/523,252, Response filed Aug. 9, 2016 to Non Final Office Action mailed May 11, 2016", 14 pgs.

"U.S. Appl. No. 14/523,252, Response filed Dec. 21, 2016 to Final Office Action mailed Oct. 6, 2016", 13 pgs.

"U.S. Appl. No. 14/523,252, Restriction Requirement mailed Dec. 24, 2014", 7 pgs.

"U.S. Appl. No. 15/804,293, Final Office Action mailed Sep. 10, 2020", 16 pgs.

"U.S. Appl. No. 15/804,293, Non Final Office Action mailed Jan. 8, 2020", 15 pgs.

"U.S. Appl. No. 15/804,293, Response filed Jun. 5, 2020 to Non Final Office Action mailed Jan. 8, 2020", 10 pgs.

(56) References Cited

OTHER PUBLICATIONS

"U.S. Appl. No. 15/804,293, Response filed Dec. 9, 2019 to Restriction Requirement mailed Oct. 8, 2019", 2 pgs.
"U.S. Appl. No. 15/804,293, Restriction Requirement mailed Oct. 8, 2019", 6 pgs.
"U.S. Appl. No. 17/173,050, Final Office Action mailed Apr. 18, 2023", 15 pgs.
"U.S. Appl. No. 17/173,050, Non Final Office Action mailed Jan. 9, 2023", 14 pgs.
"U.S. Appl. No. 17/173,050, Response filed Apr. 6, 2023 to Non Final Office Action mailed Jan. 9, 2023", 10 pgs.
"U.S. Appl. No. 17/173,050, Response filed Dec. 26, 2022 to Restriction Requirement mailed Oct. 7, 2022", 3 pgs.
"U.S. Appl. No. 17/173,050, Restriction Requirement mailed Oct. 7, 2022", 6 pgs.
"U.S. Appl. No. 18/540,537, Non Final Office Action mailed Jun. 25, 2024", 8 pgs.
"U.S. Appl. No. 18/540,537, Notice of Allowance mailed Sep. 29, 2024", 8 pgs.
"U.S. Appl. No. 18/540,537, Preliminary Amendment filed Jan. 29, 2024", 6 pgs.
"U.S. Appl. No. 18/540,537, Response filed Sep. 19, 2024 to Non Final Office Action mailed Jun. 25, 2024", 8 pgs.
"Priority document of U.S. Appl. No. 61/383,823 under PCT/US2011/052144 filed Sep. 19, 2011".
"European Application Serial No. 13784905.5, Partial Supplementary Search Report mailed Nov. 18, 2015", 8 pgs.
"International Application Serial No. PCT/US2013/032531, International Preliminary Report on Patentability mailed Nov. 13, 2014", 6 pgs.
"International Application Serial No. PCT/US2013/032531, International Search Report mailed Jul. 25, 2013", 3 pgs.
"International Application Serial No. PCT/US2013/032531, Written Opinion mailed Jul. 25, 2013", 4 pgs.
"International Application Serial No. PCT/US2013/165616, International Search Report mailed Jul. 25, 2023", 3 pgs.
"International Application Serial No. PCT/US2013/165616, Written Opinion mailed Jul. 25, 2023", 4 pgs.
"International Application Serial No. PCT/US2014/025032, International Search Report mailed Jul. 11, 2014", 2 pgs.
"International Application Serial No. PCT/US2014/025032, Written Opinion mailed Jul. 11, 2014", 5 pgs.
"Japanese Application Serial No. 2015-510279, Office Action mailed Jan. 31, 2017".
"U.S. Appl. No. 61/640,313, filed Apr. 30, 2012".
"U.S. Appl. No. 61/643,662, filed May 7, 2012".
Steffen, "Minimally Invasive Bone Harvesting Tools", Eur Spine J, vol. 9, Suppl I, (2000), 5 pgs.
"Australian Application Serial No. 2013257164, First Examination Report mailed Nov. 7, 2016", 3 pgs.
"Australian Application Serial No. 2013257164, Response filed Jul. 10, 2017 to First Examination Report mailed Nov. 7, 2016", 20 pgs.
"Indian Application Serial No. 2620 KOLNP 2014, First Examination Report mailed Jan. 30, 2020", 6 pgs.
"Indian Application Serial No. 2620 KOLNP 2014, Response filed Sep. 10, 2020 to First Examination Report mailed Jan. 30, 2020", 10 pgs.

* cited by examiner 23
24

21
22

19
20

2002
2001
2003

2002

α
2101
2102

α
2103

α
2104

2202
α
2201

2204
2203

3201
3203
3202

3201
3203
3202

3201
3203
3202

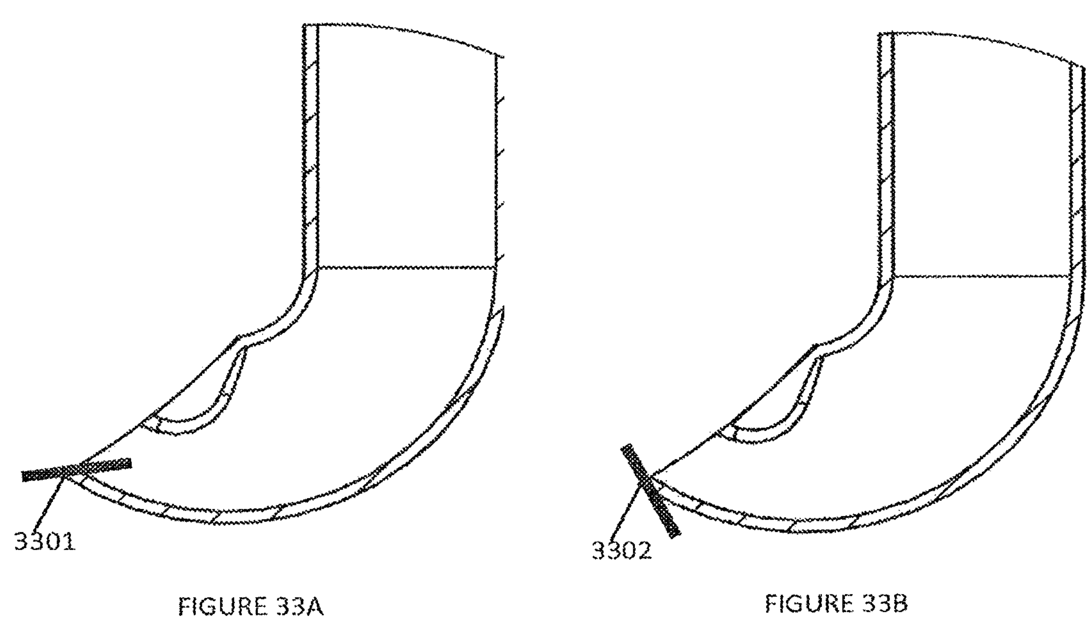
FIGURE 33A
FIGURE 33B
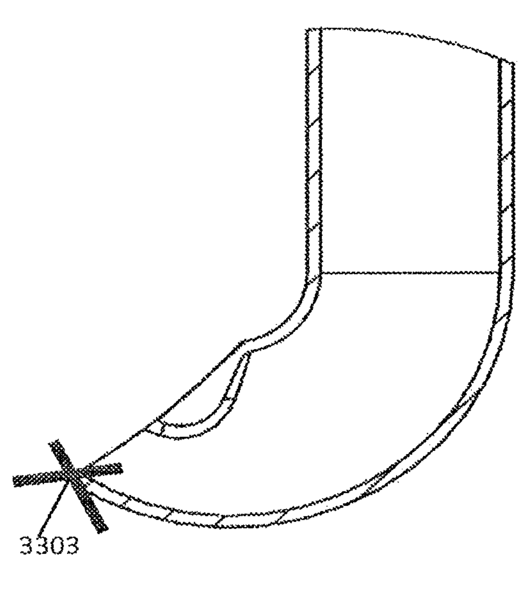
FIGURE 33C

BONE HARVESTING

CROSS-REFERENCE TO RELATED APPLICATIONS

This application is a continuation of U.S. patent application Ser. No. 18/540,537, filed on Dec. 14, 2023, which is a continuation of U.S. patent application Ser. No. 17/173,050, filed on Feb. 10, 2021, which claims priority benefit to a U.S. patent application entitled "Bone Harvesting," which was filed Nov. 6, 2017 and assigned Ser. No. 15/804,293, which was a continuation application that claimed priority benefit to a U.S. patent application entitled "Bone Harvesting," which was filed Oct. 24, 2014 and assigned Ser. No. 14/523,252 (now U.S. Pat. No. 9,833,248, issued Dec. 5, 2017), which was a continuation application claiming priority benefit to a PCT application entitled "Bone Harvesting," which was filed on Mar. 15, 2013 and assigned Serial No. PCT/US2013/032531, and which in turn claimed priority benefit to U.S. provisional patent applications designated by Ser. Nos. 61/640,313, filed Apr. 30, 2012, and 61/643,662, filed May 7, 2012, all of which are hereby incorporated by reference herein in their entirety.

SUMMARY

Methods and devices for harvesting cancellous bone are disclosed.

BACKGROUND

Bone grafts are used in surgical procedures that require the fusion, healing or joining of bones. Often bone grafts are harvested from the cancellous bone of a patient's own body, for example from the iliac crest, the fibula, the ribs, the mandible, or any other area where cancellous bone is accessible.

BRIEF DESCRIPTION OF THE DRAWINGS

FIGS. 33A-C schematically show different sharpened distal tips.

DETAILED DESCRIPTION

Figure 1:
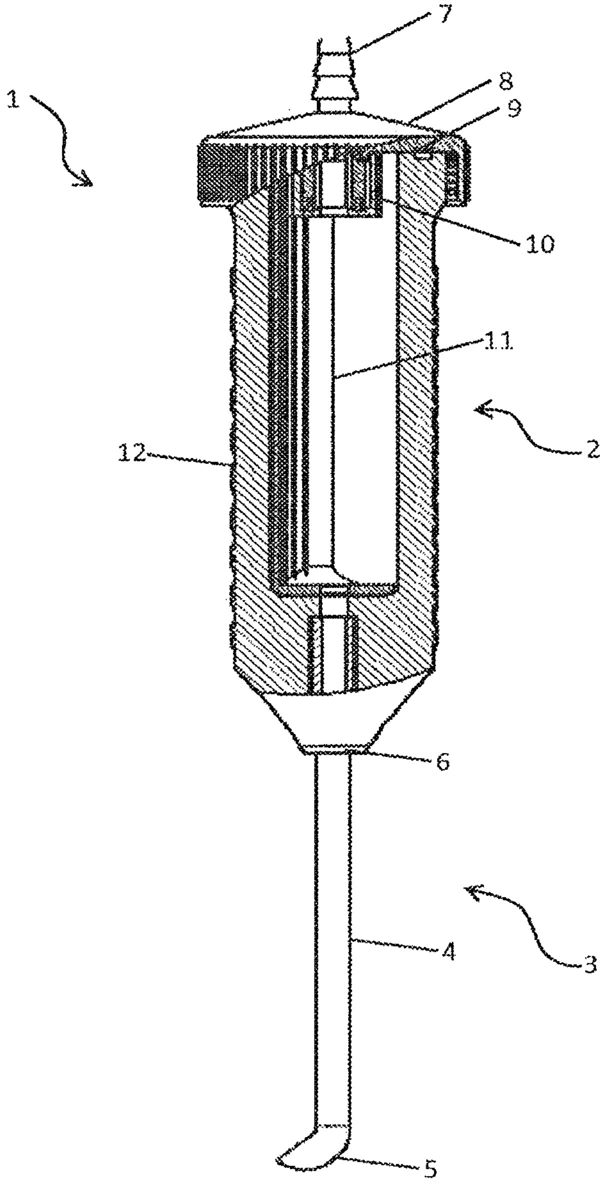
FIG. 1 schematically shows a partial cross-section of a bone-harvesting device.
Figure 24:
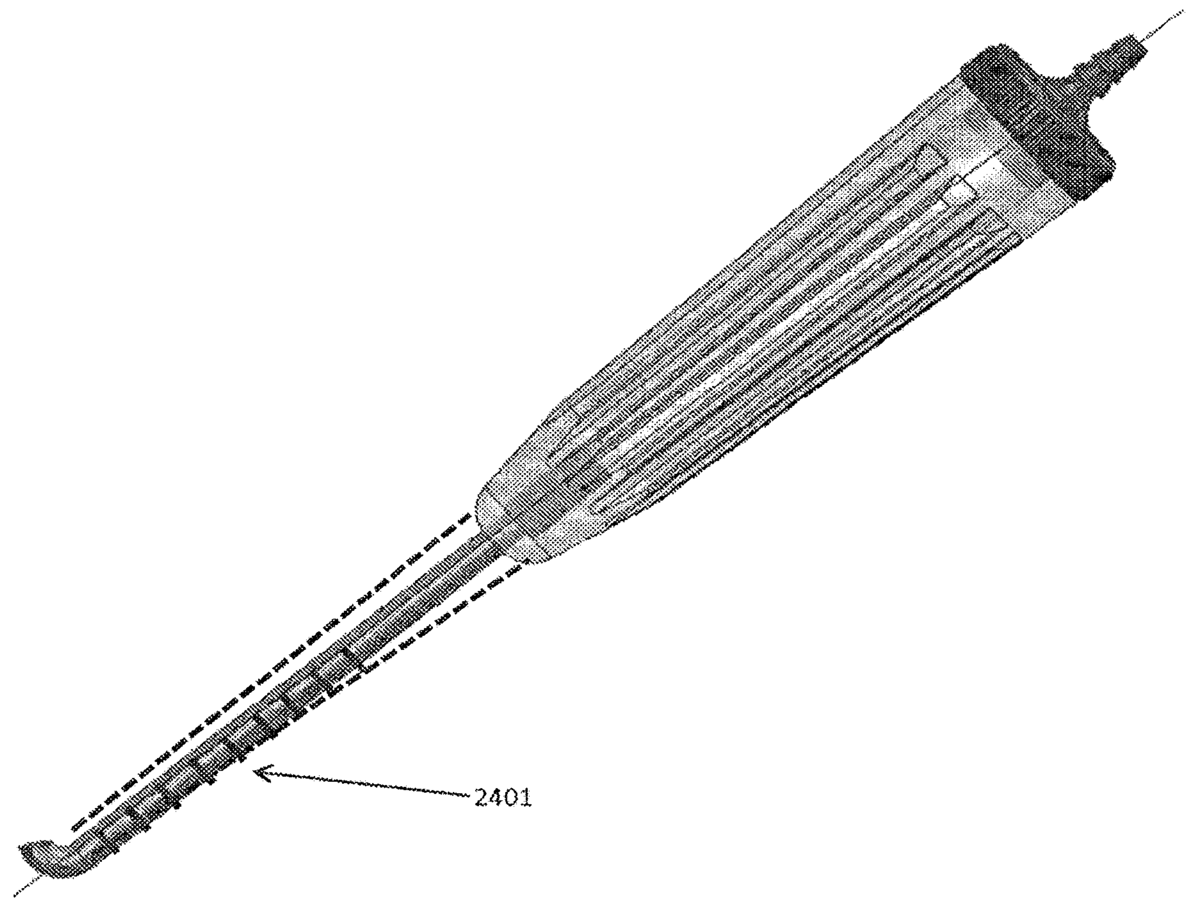
FIG. 24 schematically shows a bone harvesting device with depth markings along the tapered or non-tapered cannula.

FIG. 1 schematically shows a partial cross-section of a bone-harvesting device 1 for harvesting cancellous bone. The bone-harvesting device includes a bone receptacle 2 and a cannula 3. The cannula has a straight proximal portion 4 and a curved distal portion 5. The bone receptacle 2 has an entry port 6 connected to the cannula 3. The bone receptacle also has a suction port 7 where a suction hose can be attached so as to draw through the distal end of the cannula, through the cannula 3 and into the bone receptacle 2. In this case, the suction port 7 is formed on a cap 8 that forms an airtight seal with the bone receptacle 2 by way of an o-ring 9. Other sealing arrangements are also possible such as an interference fit, and/or built in grooves or seal designs. Inside the bone receptacle, the suction port is covered by a filter 10, designed to allow passage of blood, air and other fluid and biological materials, but not particles of bone above a certain size. The filter may pass only those bone particles whose minimum dimension is below a certain length, for example 0.5 millimeters, trapping other particles in the bone receptacle. The cap 8 may also have a plunger 11 for removing harvested bone (shown in more detail in FIGS. 8 and 8A). The exterior of the bone receptacle is textured 12 for use as a handle, although this is an optional feature. A wide variety of materials may be used for the various pieces. For example the cap 8 and bone receptacle 2 may be plastic, and the cannula 3 may be metal. In some embodiments, the device may be disposable, intended for single-use, while in other embodiments the device is reusable. The bone receptacle may be transparent so that the operator can see the harvested bone. A transparent bone receptacle may be marked with volume measurements (for example in cubic centimeters) allowing the user to measure how much bone has been harvested. Similarly, the cannula 3 can include length markings to allow the user to know how deeply the cannula 3 has been advanced as shown in FIG. 24.

Figure 2:
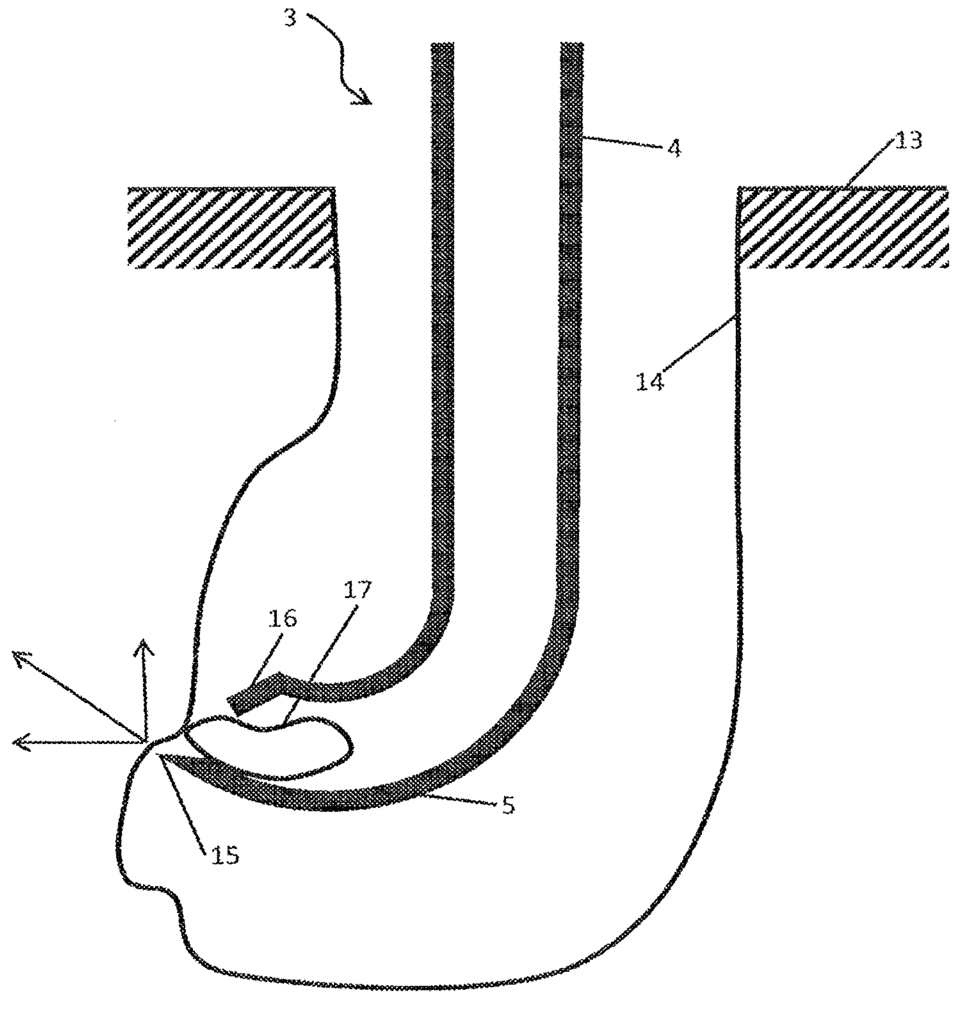
FIG. 2 schematically shows part of a bone-harvesting device harvesting cancellous bone.

FIG. 2 schematically shows part of a bone-harvesting device harvesting cancellous bone. In order to harvest cancellous bone, the cortical bone 13 is opened, for example with a drill or reamer, to reveal the underlying cancellous bone 14. In opening the cortical bone, the surgeon may also create a cavity in the cancellous bone. This access hole only needs to expose the cancellous bone in the boney region before the bone-harvesting device can be used. The cannula 3 is then advanced into the cavity.

The bone harvesting device has a hollow cannula with a straight proximal portion 4 and a curved distal portion 5. In some embodiments the cross-sectional geometry of the proximal portion 4 changes along its length, for example it may be tapered; as shown the cross-section geometry of the proximal portion 4 is constant along its length. (See FIGS. 19A and B.) Part of or all of the distal tip of the cannula is sharpened to form a cutting edge 15. This cutting edge can be all or a portion of the circumference of the distal portion 5. This tip can be sharpened from the outer wall, inner wall or both directions as shown in FIGS. 33A-C. The distal end of the hollow cannula may be partially occluded by an occluding member 16. The user would initiate a pilot hole using standard tooling such as a reamer or trephine to create a small access hole to expose the cancellous region of the boney region. Once the cancellous region is exposed, the bone harvesting device is ready to be inserted. The user advances the distal cutting tip into the access hole and initiates small rotational strokes to advance the device deeper into the boney space while enlarging the cavity. As the cavity enlarges the user can advance the bone harvesting device into the bone cavity, moving it laterally so that the cutting edge 15 contacts the cancellous bone wall of the cavity, and pulling the bone-harvesting device upward, so that the cutting edge 15 scrapes a portion of cancellous bone 17 into the bone-harvesting device to be harvested. The bone-harvesting device features and enables the user to implement rocking, scraping, curetting, carving and rotational cutting strokes. The harvested portion of cancellous bone 17 is pulled up through the cannula by the application of suction at the proximal end of the cannula (not shown in FIG. 2). The harvested portion of cancellous bone 17 will necessarily fit through the cannula because the occluding member 16 limits the size of the bone portion that enters the distal portion 5. This helps to prevent clogs. The cannula 3 may have constant cross-sectional size and shape, or it may taper along its length. For example, the cannula may have circular cross-sectional shape with the proximal portion larger than the distal portion. The proximal portion may be a steep conical frustum. Tapering the cannula to larger cross-sectional area more proximally may also help to prevent clogs. The combination of tapering and the occluding plate member helps avoid clogging of the device.

Figure 3:
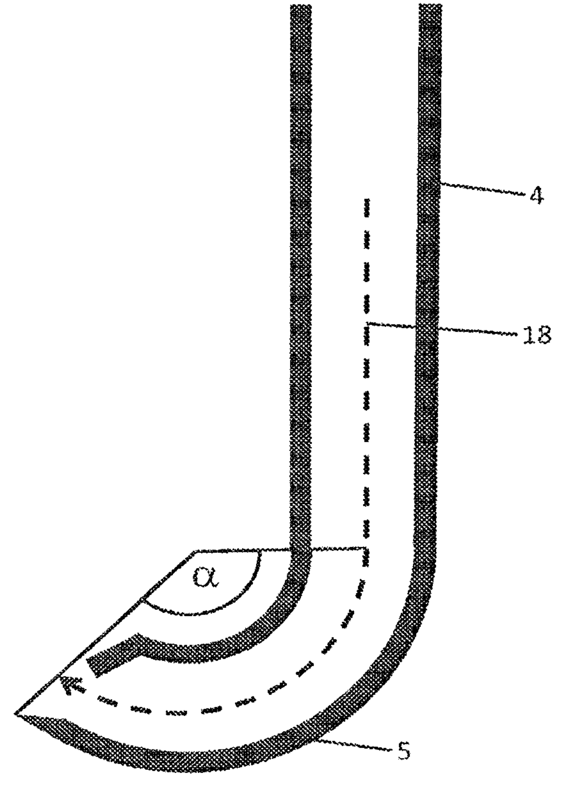
FIG. 3 schematically shows the curved distal portion of a bone-harvesting device.
Figure 14:
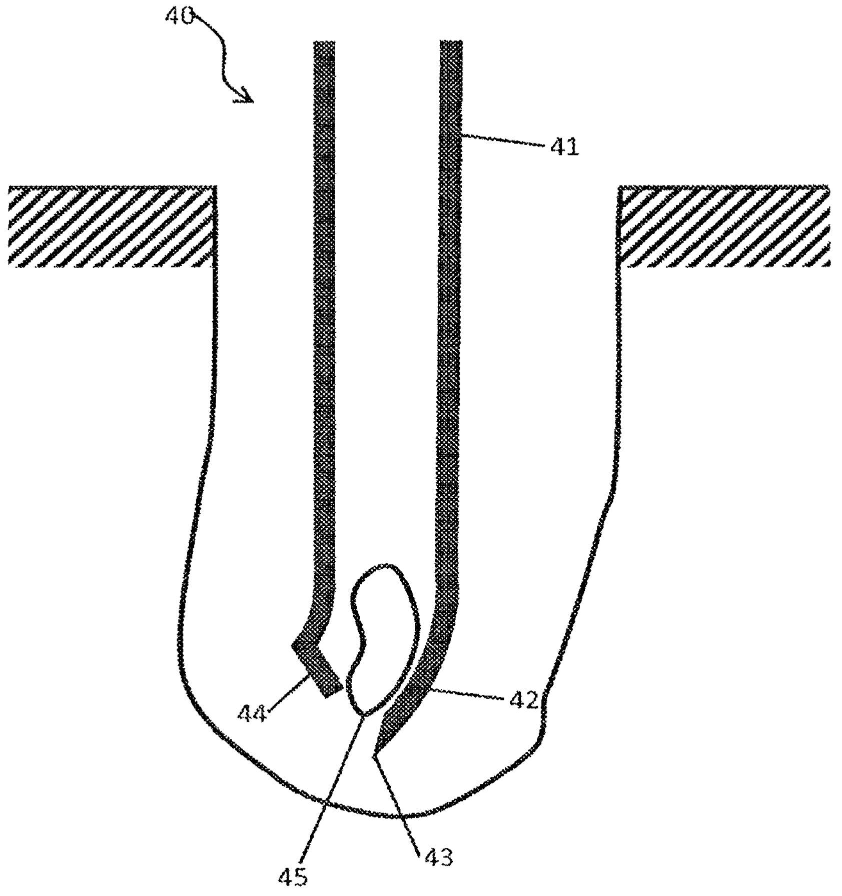
FIG. 14 schematically shows another embodiment of a distal tip of a cannula.
Figures 15, 16:
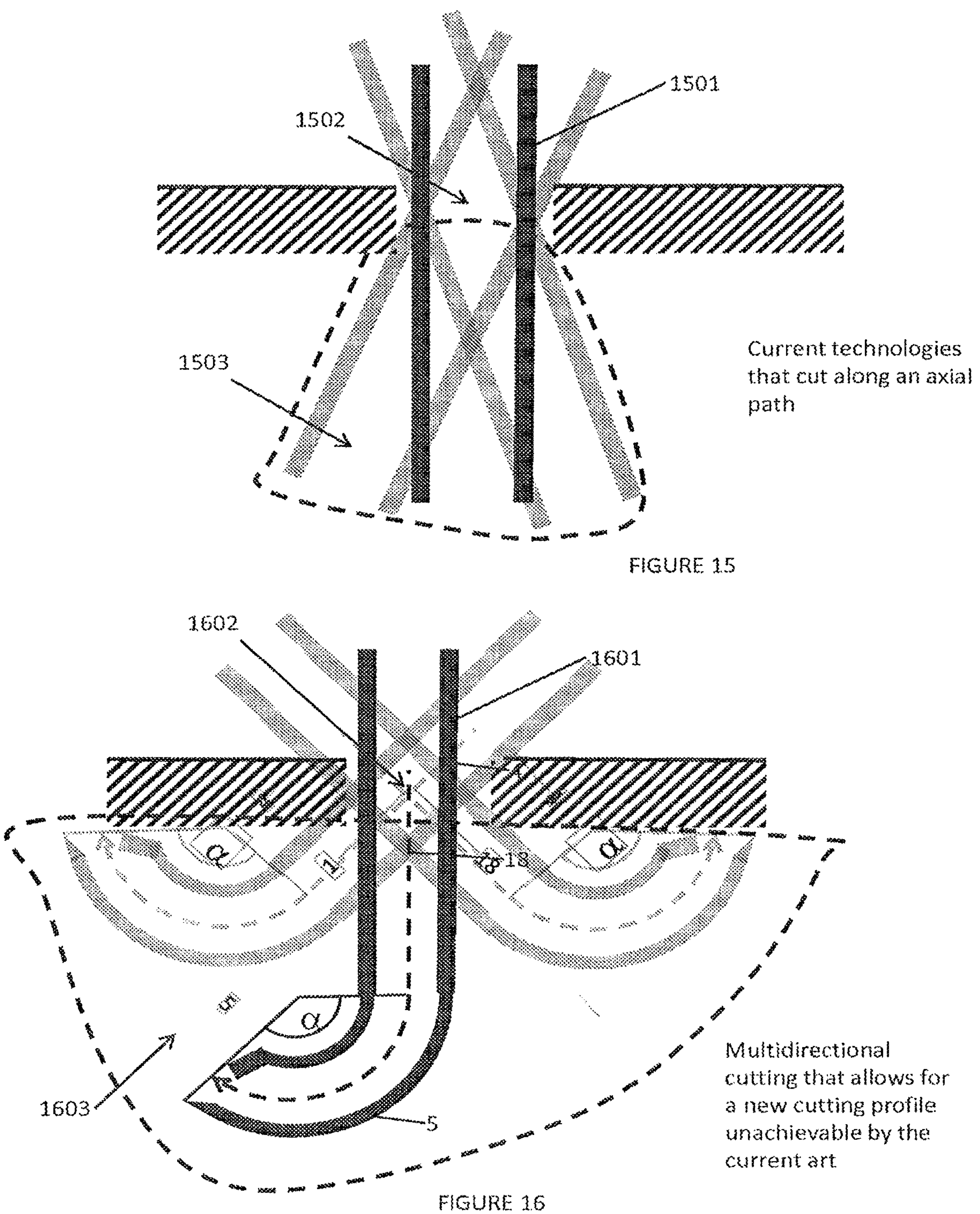
FIGS. 15, 16 and 17A-C schematically show different cavities excavated by different bone harvesting devices.

FIG. 3 schematically shows the curvature of the curved distal portion 5. The straight proximal portion 4 defines an axis 18. The distal portion 5 curves through an arc whose angular extent is labeled α. As shown in FIG. 3, α is about 135 degrees. Other embodiments may include distal portions that curve through an arc whose angular extent is in the range of 90 to 180 degrees, 100 to 170 degrees, 110 to 160 degrees, 120 to 150 degrees, or 130 to 140 degrees. Alternative embodiments may include a distal portion that curves through an arc whose angular extent is less than 90 degrees (as shown in FIG. 14, for example). Existing bone-harvesting devices typically do not curve through any arc at all, i.e., they have an angle α of zero degrees, so that the cutting edge is simply the lower end of a straight cannula. Enabling the plane of cutting to extend past 90 degrees enables the aforementioned cutting strokes as well as the capability to achieve a cavity profile as shown in FIGS. 16 and 17.

Figures 4, 5, 6:
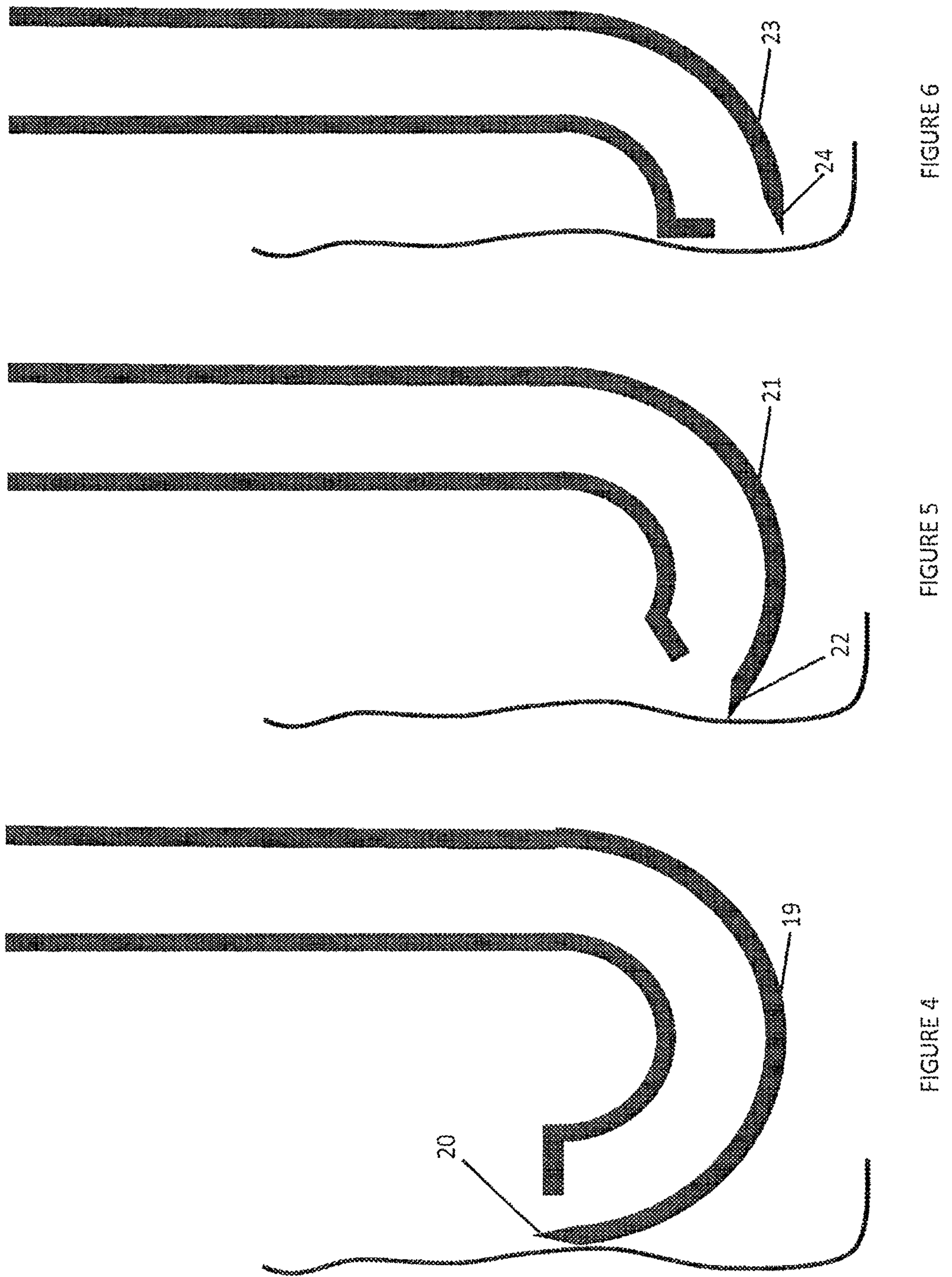
FIGS. 4-6 schematically show three bone-harvesting devices with different curved distal portions.

FIGS. 4-6 schematically show three bone-harvesting devices with different curved distal portions. FIG. 4 schematically shows a distal portion 19 that curves through an arc of 180 degrees. In this 180-degree embodiment, the sharpened cutting edge 20 is shown facing directly upward. When applied to a vertical cavity wall and pulled upward by the user, the vertical cutting edge 20 cannot apply any horizontal force to the wall of the cavity; there is no horizontal component to the action of the cutting edge 20. FIG. 5 schematically shows a distal portion 21 that curves through an arc of about 135 degrees. When applied to a vertical cavity wall and pulled upward by the user, the cutting edge 22 includes components that are both vertical and horizontal, so that the cutting edge 22 can cut both into the wall and also upward along the surface of the wall. FIG. 6 schematically shows a distal portion 23 that curves through an arc of just 90 degrees. When applied to a vertical cavity wall and pulled upward by the user, the horizontal cutting edge 24 is directed perpendicular to the motion and therefore will not cut into the cavity wall at all, instead just sliding along the surface. A distal portion that curves through an arc of more than 90 degrees but less than 180 degrees will be preferred for some applications. With such a curve, when the user forces the distal end of the bone-harvesting device against the cavity wall and drags the bone-harvesting device upward, the cutting edge will contact with the cavity wall with both a horizontal component, allowing the cutting edge some purchase on the cancellous bone, and also a vertical component, allowing the cutting edge to peel cancellous bone off the cavity wall.

Figure 7:
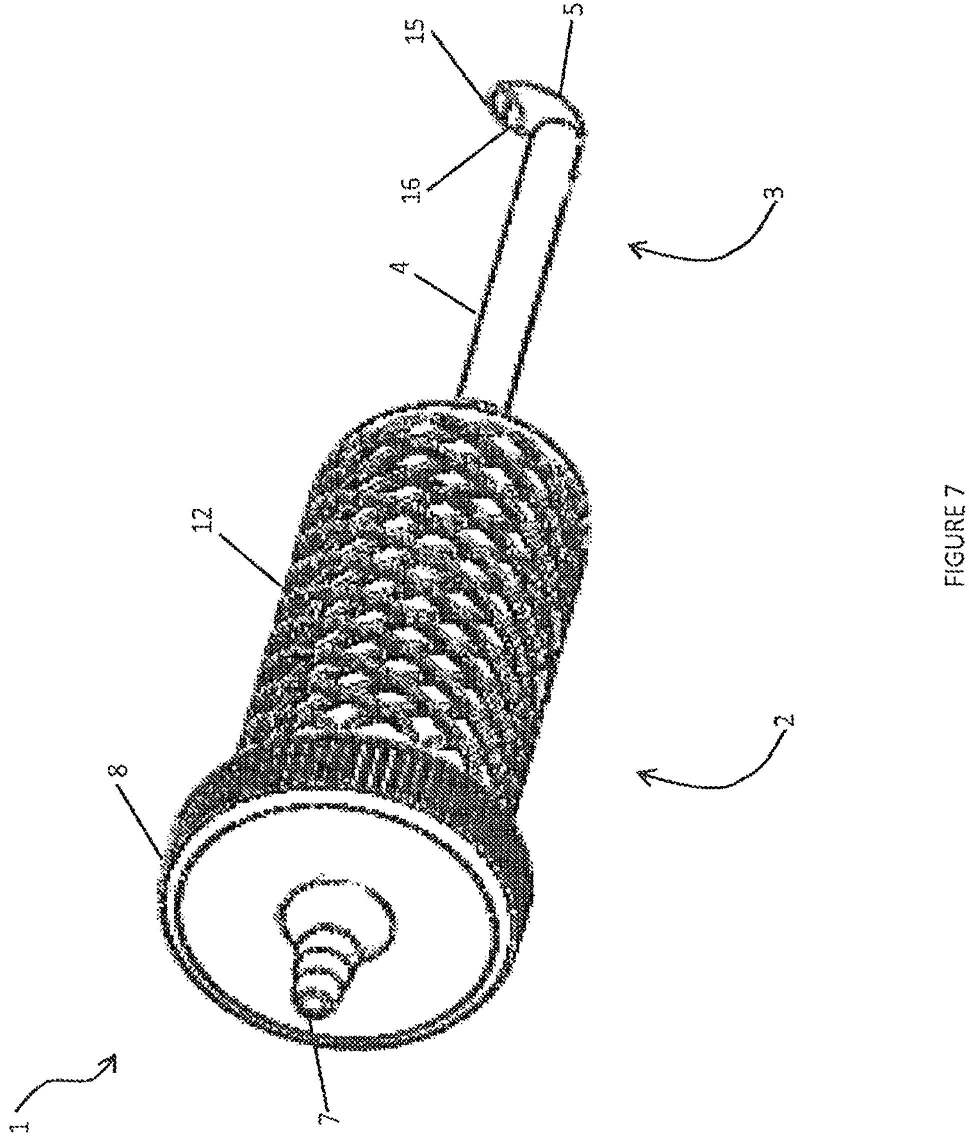
FIG. 7 schematically shows a perspective view of the exterior of a bone-harvesting device of FIG. 1.

FIG. 7 schematically shows a perspective view of the exterior of the same bone-harvesting device 1 as FIG. 1, showing the bone receptacle 2, the cannula 3, the straight proximal portion of the cannula 4, the curved distal portion of the cannula 5, the suction port 7, the cap 8, the textured handle 12, the cutting edge 15, and the occluding member 16.

Figure 8:
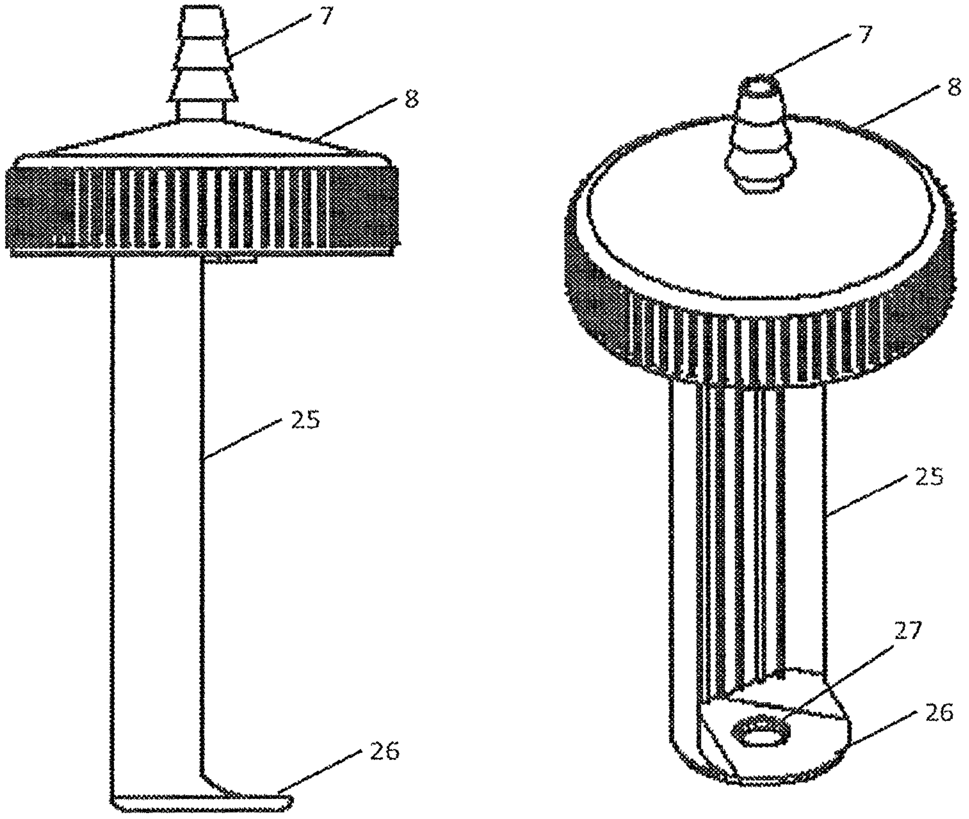
FIG. 8 schematically shows the cap shown in FIG. 1.

FIG. 8 schematically shows in more detail and in two perspectives, the cap 8 of FIG. 1. The suction port 7 is visible on the exterior of the cap 8. The interior of the cap 8 can include a plunger 25. Harvested cancellous bone is pulled through the cannula under suction and passes from the cannula into the bone receptacle through the plunger plate 26 by way of an opening 27. To remove harvested bone from the bone receptacle, the user can unscrew the cap 8 and lift the bone out of the receptacle contained by the plunger 25 and the plunger plate 26. Alternatively, the cap may be secured to the receptacle by any other useful method such as a latch, an interference fit, clips, etc.

Figure 8A:
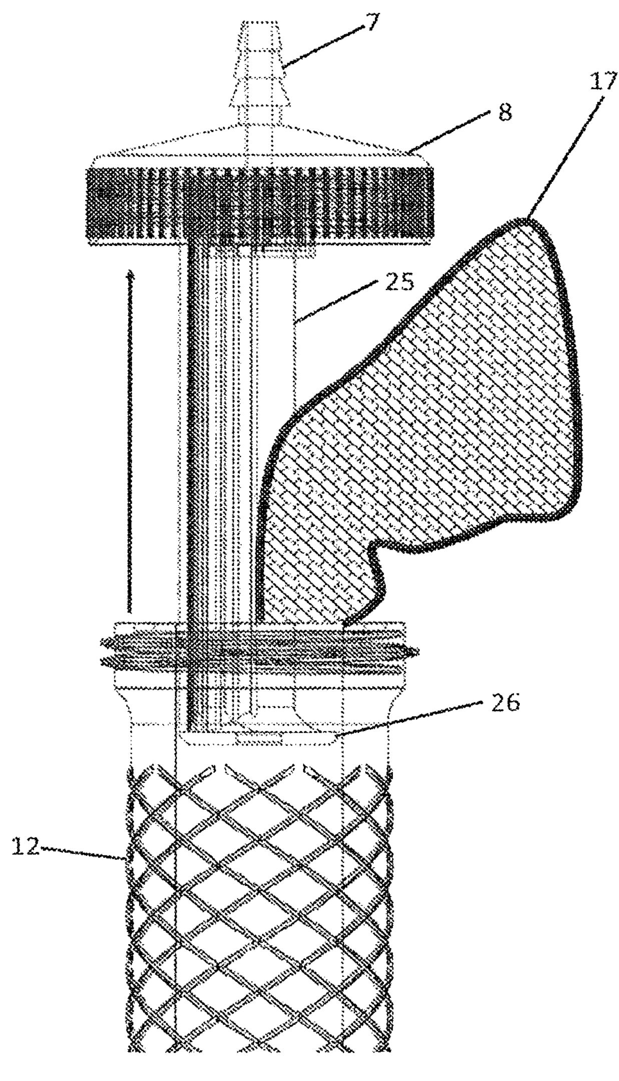
FIG. 8A schematically shows the cap shown in FIG. 1 in use.
Figure 8B:
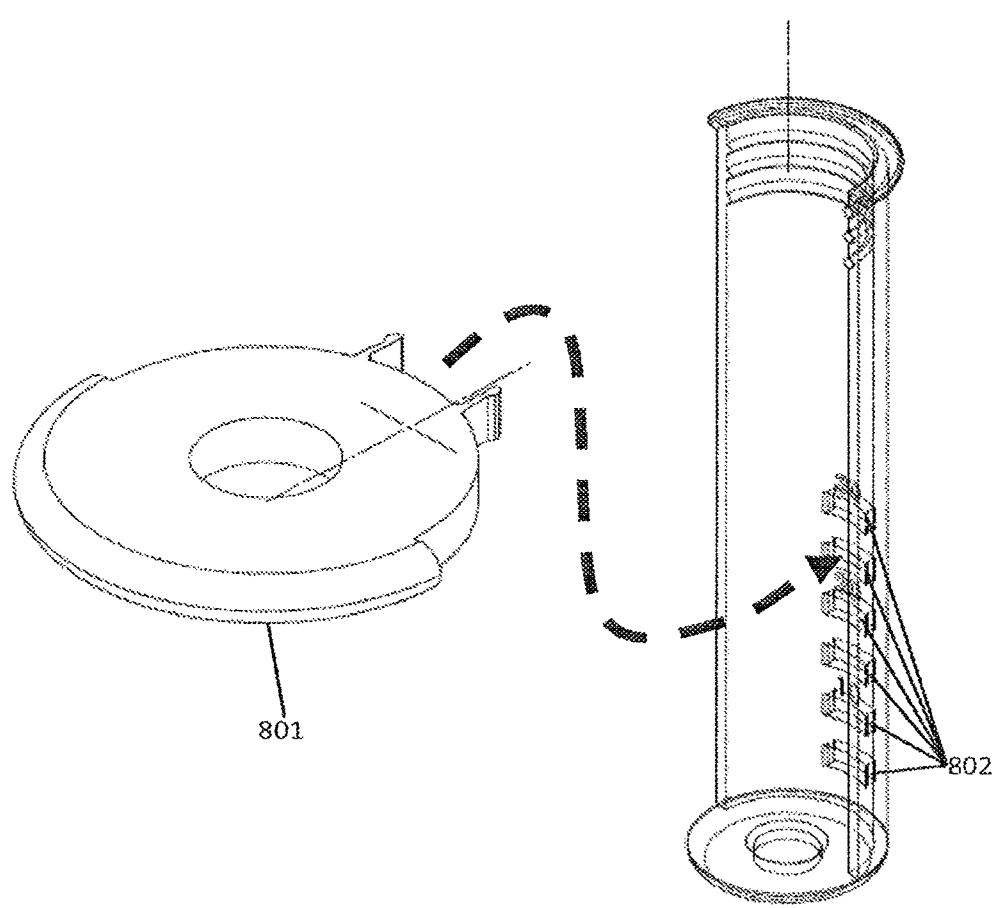
FIGS. 8B-8E schematically show a separate volume-adjustable plunger.

FIG. 8A schematically shows the cap shown in FIG. 1 in use. Once the cancellous bone 17 has been harvested, the cap 8 can be unscrewed from the bone receptacle and handle 12. As the cap 8 and its plunger 25 and plunger plate 26 are lifted out of the bone receptacle (in the direction marked by the arrow), the cancellous bone 17 is lifted out along with the cap 8 contained by the plunger 25 and plunger plate 26. In embodiments lacking a plunger, the cap is unscrewed and an elongated tool such as an osteotome can be utilized to scoop out the bone from the bone receptacle.

Figure 8C:
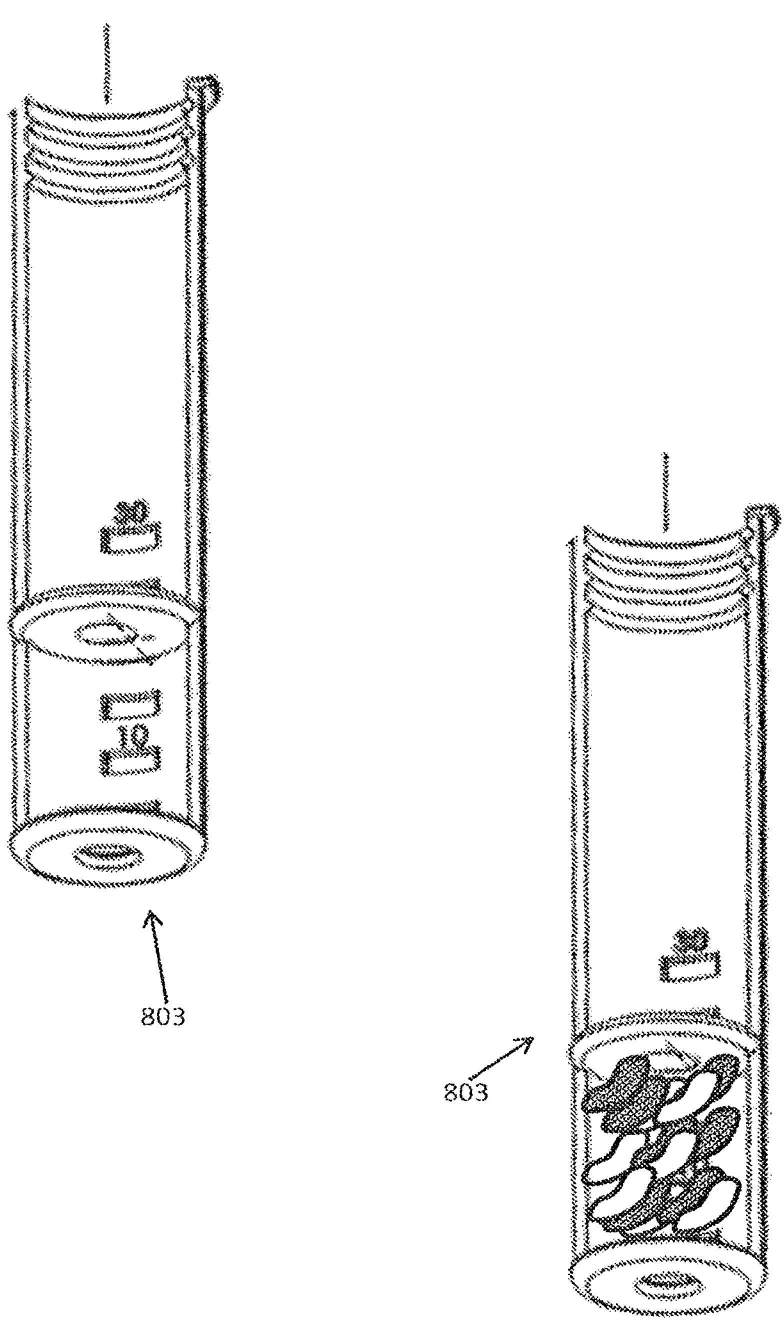
Figure 8D:
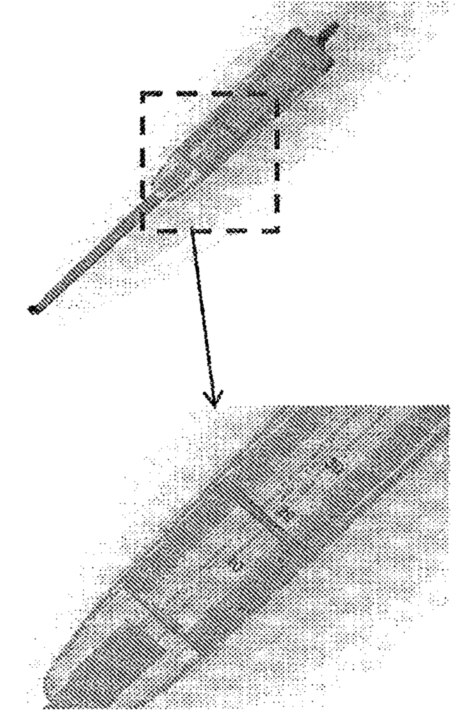
Figure 8D:
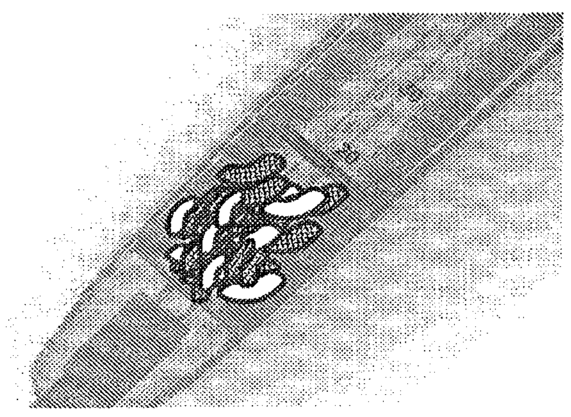
Figure 8E:
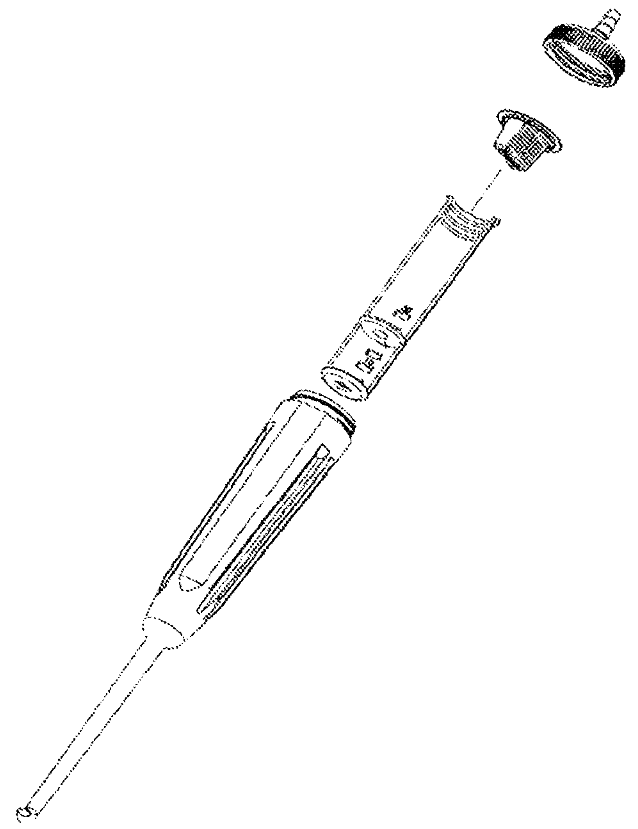

FIGS. 8B-8E schematically show a separate volume-adjustable plunger. A stop disc 801 can be snapped into a variety of slots on plunger 802 to define a desired volume. The disc can be alternatively thread, groove fit, male to female connect, or interference fit into place. With the disc 801 installed, the plunger 803 defines a chosen volume to be filled with harvested bone. FIG. 8C shows the plunger 803 empty and filled with harvested bone. FIG. 8D shows a closeup of the assembled plunger from outside the bone harvester, and, schematically, the plunger filled with harvested bone. FIG. 8E shows an exploded device including the volume-adjustable plunger and stop disc. The bone-harvesting device without said plungers and only a cap, or any of the preceding plungers can also be used with a bone packing accessory to push the bone to the bottom of the bone receptacle thereby facilitating bone volume measurement.

Figure 9A:
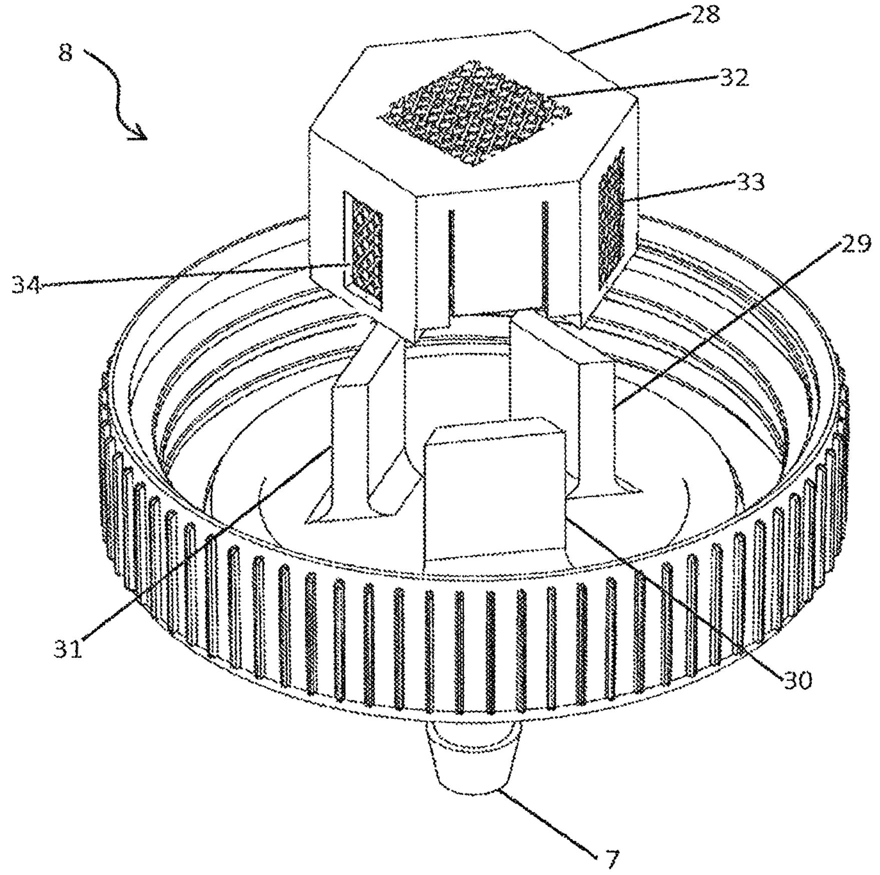
FIGS. 9A and 9B schematically show the underside of the cap shown in FIG. 8.

FIG. 9A schematically shows the underside of a cap 8 with a filter 28. As shown, the filter is a separate piece that snaps on to posts 29, 30, 31, but the filter may also be integral with the cap 8. In this case the filter includes sieves 32, 33, 34 (a fourth is not visible on the back side of the filter), but may include any number. This filter fully covers the entrance to the suction port inside the cap 8, so that fluid (for example blood, or air) passing to the suction port 7 must travel through the sieves 32, 33, 34. The sieves 32, 33, 34 are fine enough to capture and prevent passage of bone particles above a certain size. For example, the sieves 32, 33, 34 may be sized so that all bone particles whose smallest dimension is greater than 0.5 millimeters are caught by the sieves 32, 33, 34 and remain in the bone receptacle even when the receptacle is under suction. Alternatively, the bone receptacle may be designed for operation without any filter by tuning the suction flow rate and the interior geometry of the bone receptacle to trap bone particles of a particular size range.

Figure 9B:
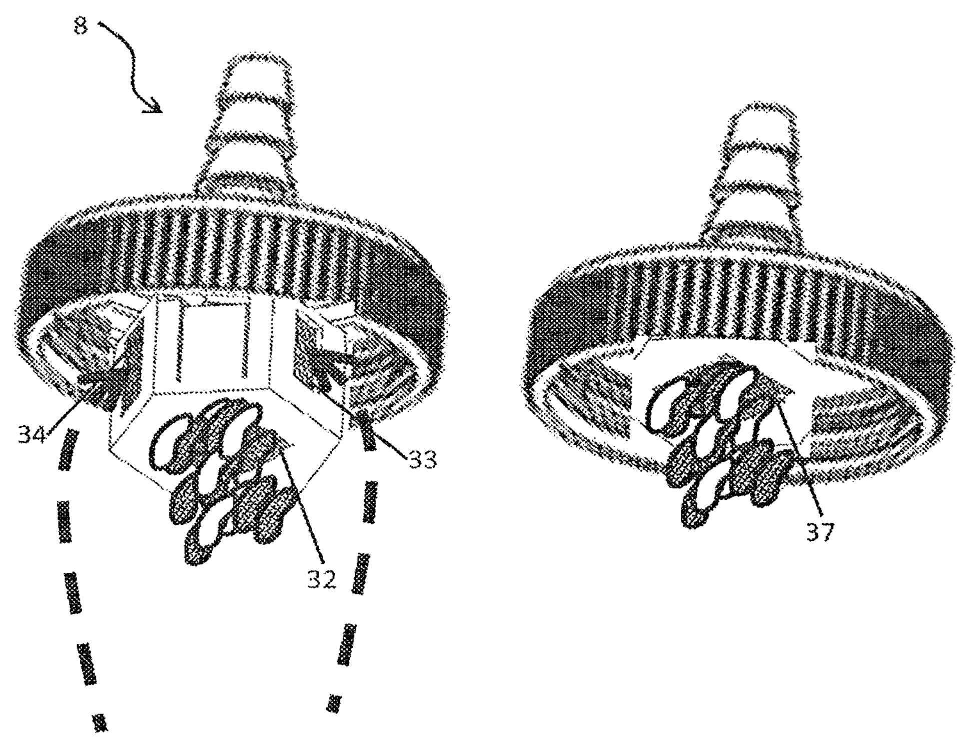

FIG. 9B schematically shows the underside of such a cap 8 with trapped bone pieces. The multiple sieves allow for one sieve 32 to be clogged with bone pieces while the other or others 33, 34 remain free to maintain suction. In a cap with only a single sieve 37, a single clog can block suction. By including sieves having different orientations, some sieves can remain clear while others may be blocked by large particles. As shown, the filter includes at least two sieves (in this case four) no two of which are parallel. The filter could include non-planar sieves, such as sieves having an undulating or sinusoidal form, or a single sieve structured so that parts of it can remain clear while other parts may be blocked. For example, a filter consisting of a single sieve could have a sieve in the form of a geometric prism, or a hemisphere or the like.

Figure 10:
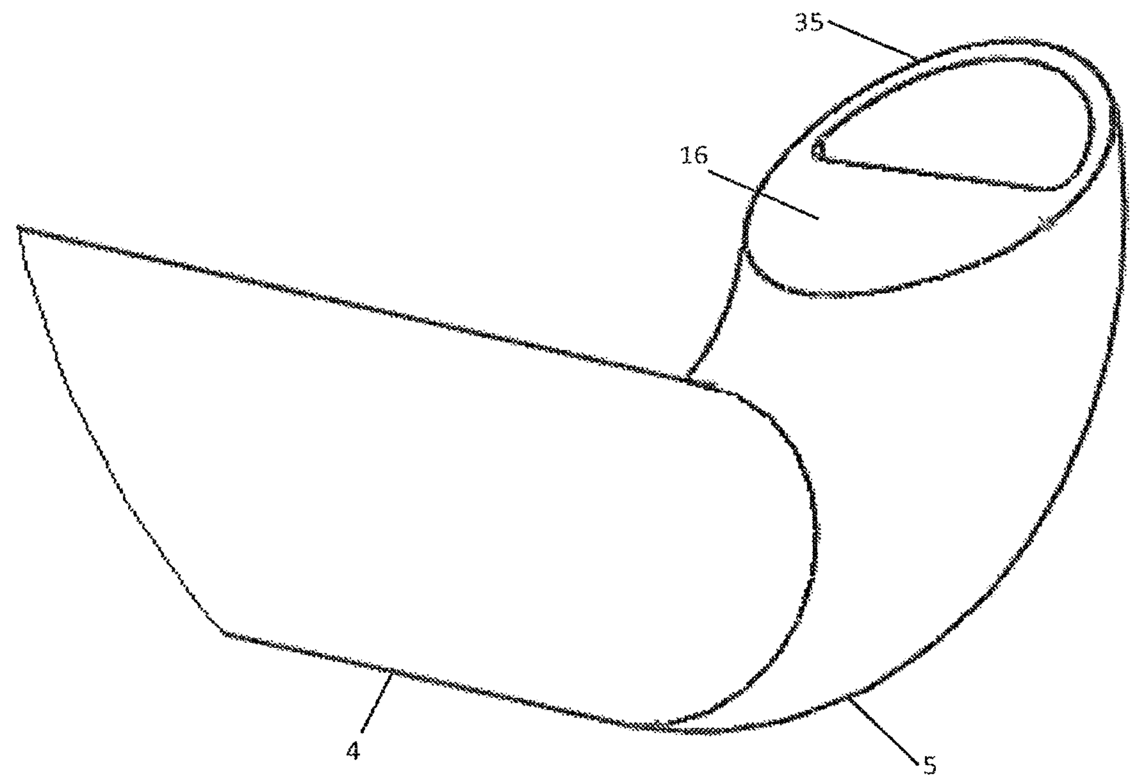
FIG. 10 schematically shows an embodiment of the distal end of a cannula in a bone-harvesting device.

FIG. 10 schematically shows an embodiment of the cannula 4. In use, the cannula will typically have a sharpened cutting edge. During manufacturing, the cannula 4 may be formed with a relatively blunt edge 35 that can be later sharpened. It can be sharpened from various directions as shown in FIGS. 33A-C. The occluding member 16 can either be integral with the rest of the cannula, as shown in FIG. 10, or can be a separate piece that is affixed to distal portion of the cannula 4. The sharpness of the cutting edge may be calibrated to make it easy for a user to cut through cancellous bone, but difficult or impossible to cut through cortical bone. This is a safety feature that will help a user to only harvest the desired cancellous bone, and keep the opening in the cortical bone as small as possible so as to keep the procedure minimally invasive. The cutting edge is tuned to provide tactile feedback for the user to be able to discern between cortical and cancellous bone.

Figure 11:
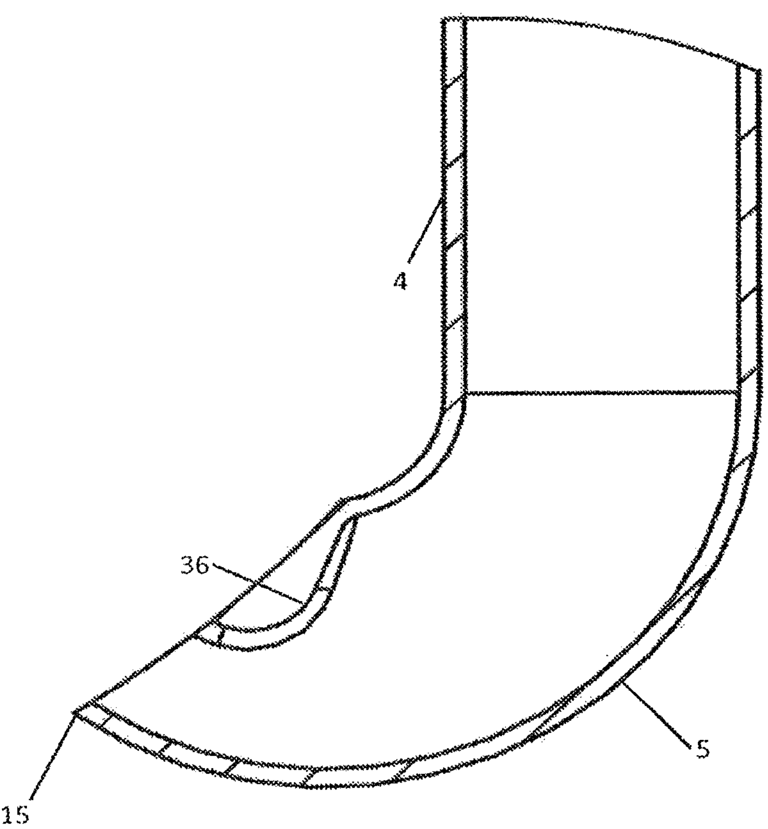
FIG. 11 schematically shows a cross section of an embodiment of the distal end of a cannula in a bone-harvesting device.

FIG. 11 schematically shows an embodiment of the distal portion 5 of the cannula 4. In this embodiment, the occluding member 36 is not planar, as shown in other embodiments, but instead is curved. In some contexts, the curvature may help to prevent bone from getting stuck on the occluding member 36.

Figure 12:
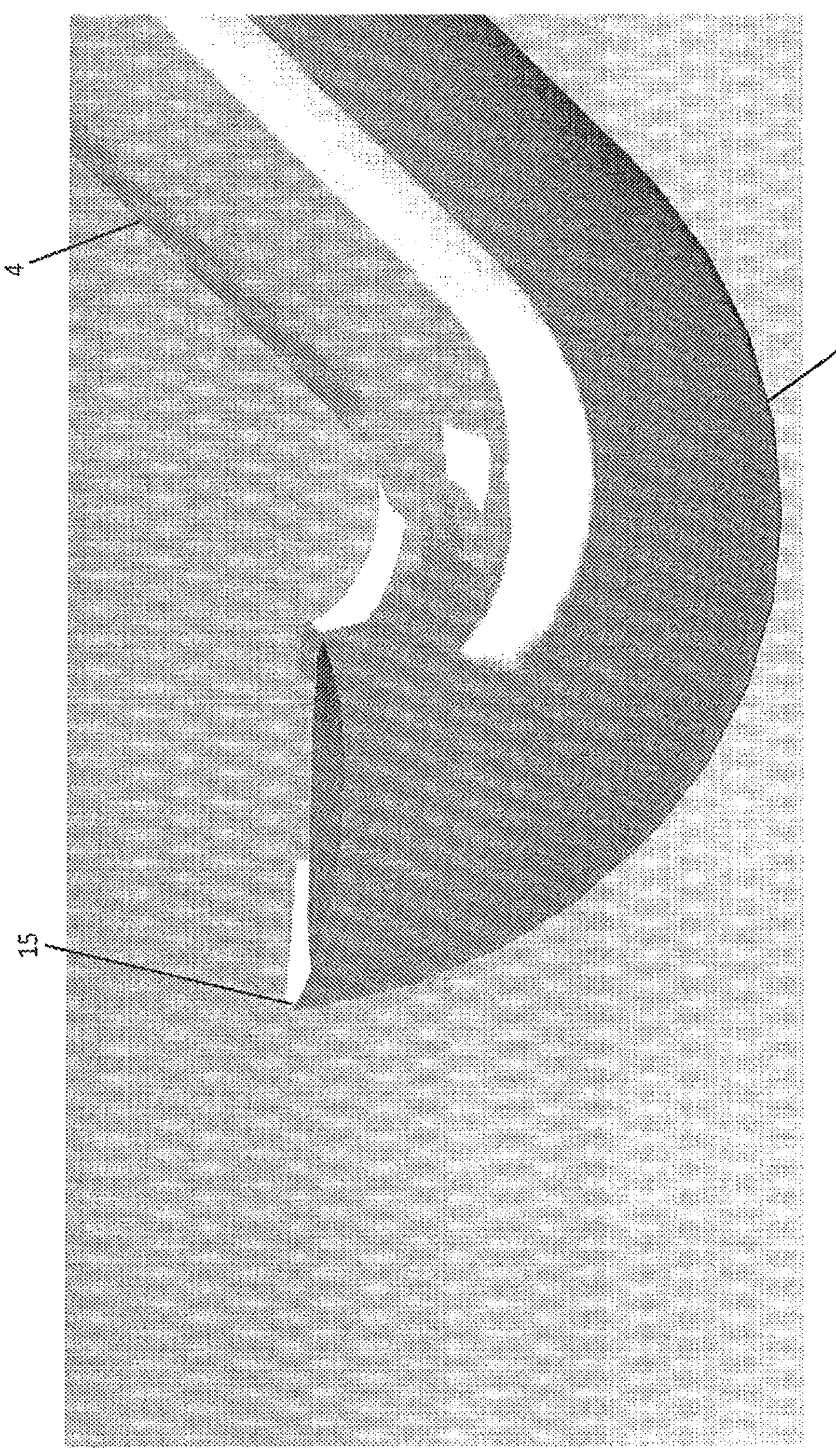
FIG. 12 schematically shows the distal portion of a cannula with no occluding member.
Figure 13:
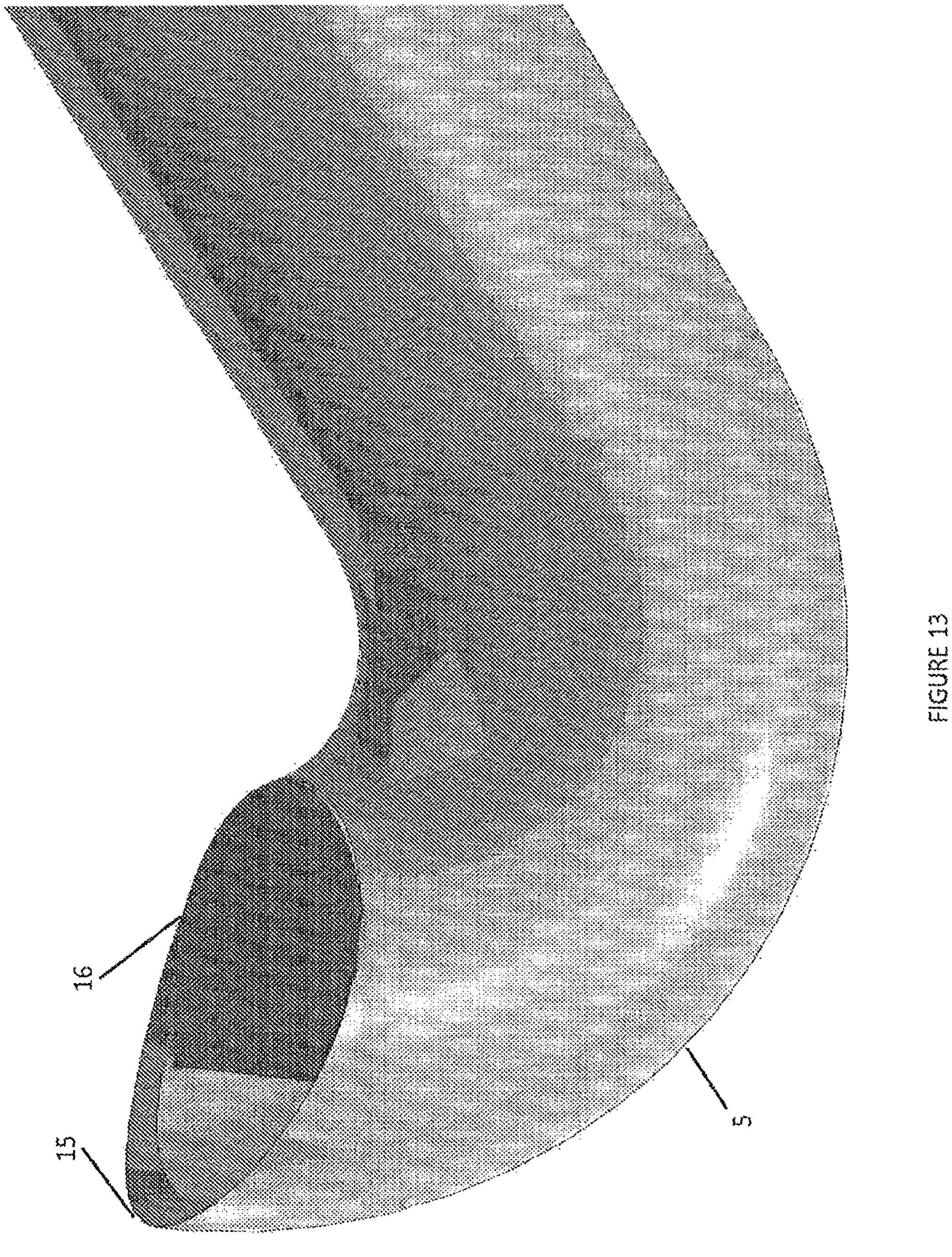
FIG. 13 shows the distal portion of a cannula with an occluding member attached.

FIG. 12 schematically shows the distal portion 5 of the cannula with no occluding member. The cutting edge 15 is shown sharpened. FIG. 13 shows the same distal portion 5 of the cannula with an occluding member 16 attached and partially occluding the distal end of the cannula. While the occluding member 16 can help to prevent clogs by limiting the size of harvested bone pieces entering the cannula, it is not necessary to the functioning of the bone-harvesting device. The bone-harvesting device as shown in FIG. 12, with no occluding member, may be preferred in certain situations.

FIG. 14 schematically shows a cannula 40 with a straight proximal portion 41 and a curved distal portion 42. The curved distal portion 42 has a cutting edge 43 at its tip, and an occluding member 44. Unlike the embodiment shown in FIG. 1, the embodiment of FIG. 14 includes a distal portion 42 that curves through an arc whose angular extent is less than 90 degrees but more than 0 degrees. This curved distal portion allows the user to harvest cancellous bone 45 using a downward motion, advancing the distal tip into the cancellous bone, rather than harvesting the bone by dragging the tip upward toward the user. The occluding member may be an optional feature to this embodiment; however, the inclusion of this feature is expected to improve the performance.

In some embodiments, the cancellous bone is cut only with the cutting edge of the distal tip. But other embodiments may include additional cutting technologies, for example, ultrasonic vibration, supersonic vibration, piezoelectric microvibration, or abrasive water jet cutting.

The device can also include technology to allow the user to sense how the distal tip is interacting with the bone, even when the tip cannot be directly visualized, for example, by use of an infrared or visible light camera, possibly an endoscopic camera, ultrasound visualization, piezoelectric sensors, or pressure or force sensors. Any such sensors can provide feedback to the user.

Figures 19A, 19B:
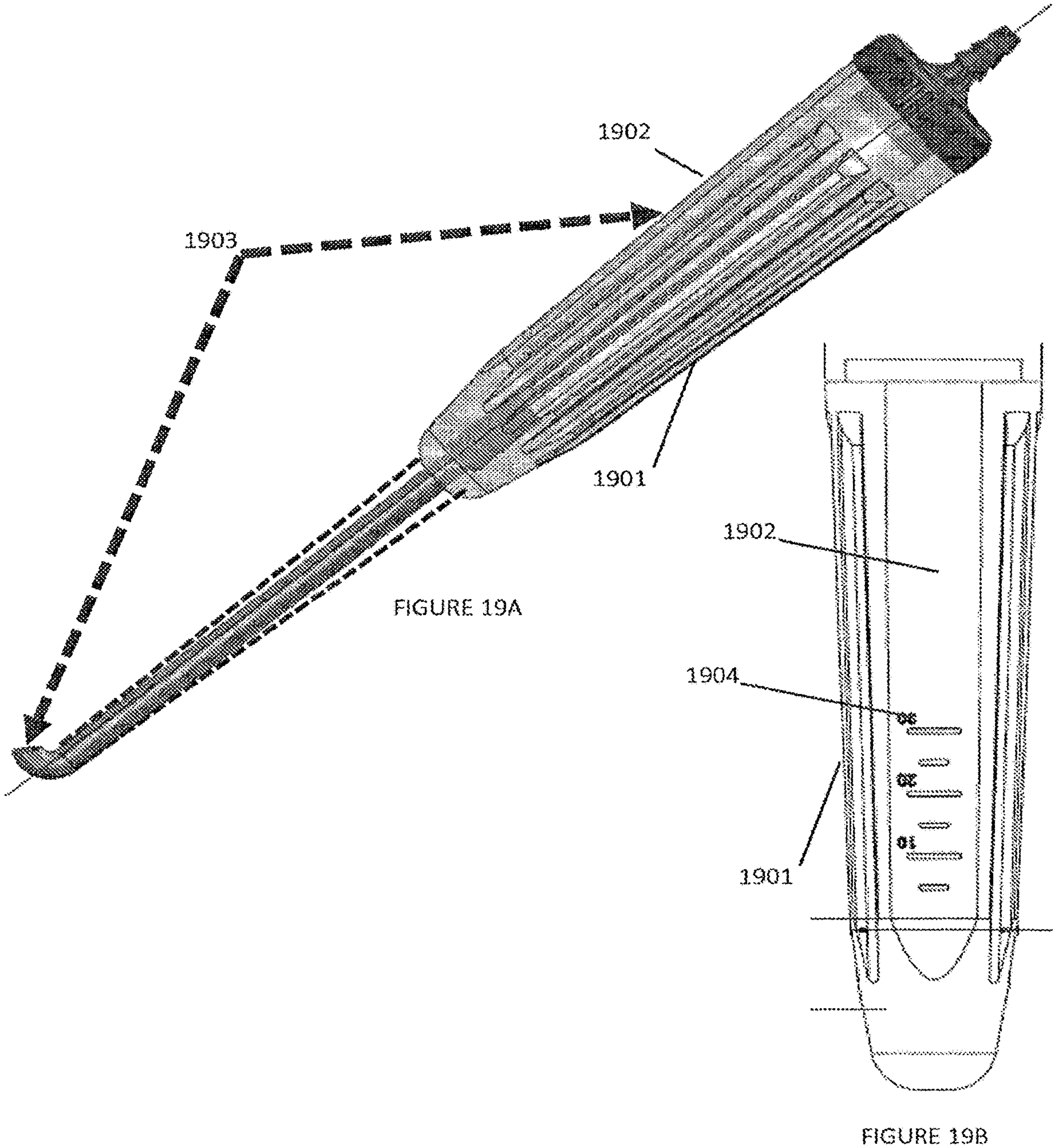

The device can also include indicia that may allow the user to know the orientation of the cutting edge and the curved distal portion, even when the distal portion cannot be directly visualized. The indicia may be structural, or drawn, etched, painted, etc., onto a handle portion, so that the user may perceive, for example by sight or feel, the orientation of the hidden distal tip of the device as shown in FIGS. 19A and B.

The cutting edge can have varying geometry such that, when the tip is moved in one direction a certain type of cutting motion is executed, while a different cutting motion is executed on a stroke in a different direction.

The cannula can include a low-friction coating on its interior to improve passage of harvested bone through the cannula into the bone receptacle. Possible coatings include Teflon® PTFE, Teflon® TFE, Teflon® S, Teflon® FEP, Teflon® PFA, Eclipse®, Dykor®, Xylan®, Xylan® XLR, Xylar®, Xylac®, various ceramics, the TEC-thermcote family of materials, and the TEC-fluorcote family of materials.

In some embodiments, a bone-harvesting device can include a cannula and a bone receptacle. The cannula can include a proximal end, a straight proximal portion, adjacent to the proximal end, that defines an axis, a curved distal portion that bends through an angle of at least 90 degrees and no more than 180 degrees relative to the axis, a distal end, adjacent to the distal portion, at least a part of the distal end being sharpened to form a cutting edge, and an occluding member that partially, but not fully, occludes the distal end. The bone receptacle can include a suction port and an entry port. The entry port can be attached to the proximal end of the cannula such that, when suction is applied to the suction port, the suction draws from the distal end of the cannula, through the cannula, and into the bone receptacle. In other embodiments, the curved distal portion can bend through an angle of more than 0 degrees but less than 90 degrees.

In some embodiments the cannula can include a proximal end, a straight proximal portion, a curved distal portion, a distal end adjacent to the distal portion, at least a part of the distal end being sharpened to form a cutting edge, and an occluding member that partially, but not fully, occludes the distal end. The bone receptacle can include a suction port, an entry port, and a filter that (a) fully covers the suction port, (b) is permeable to fluid, and (c) is impermeable to particles of cancellous bone whose smallest dimension is more than 0.25 millimeters in size (for example). The entry port can be attached to the proximal end of the hollow cannula such that, when suction is applied to the suction port, the suction draws from the distal end of the cannula, through the cannula, and into the bone receptacle.

FIGS. 15 and 16 schematically show one difference between prior art bone harvesters and the device shown in FIG. 2. FIG. 15 shows a bone harvester with no curve in the distal portion. The straight distal portion 1501 can pivot in the pilot hole 1502. But no matter how it is turned about its axis, the straight distal portion 1501 cannot harvest bone the is not directly visible along a straight line of sight through the pilot hole within the range of angles through which is it possible to pivot the straight distal portion 1501. The resulting cavity 1503 is generally conical. As shown in FIG. 16, a curved distal end 1601 like the one shown in FIG. 2, can harvest a much larger volume of bone. Similar to the straight distal end 1501, the curved distal end 1601 can pivot in the pilot hole 1602. But because of the curve, the curved distal end can be advantageously turned about its axis to excavate otherwise unreachable cancellous bone. The resulting cavity 1603 can be larger and can include regions not visible along any line of sight through the pilot hole 1602.

Figure 17A:
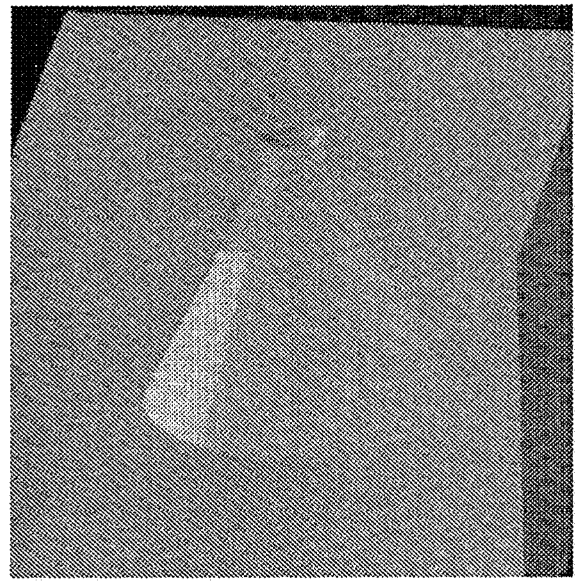
Figure 17B:
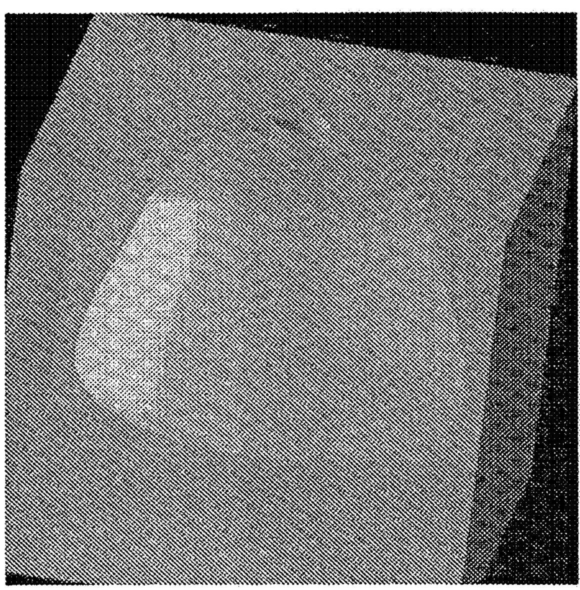
Figure 17B:
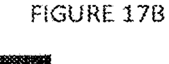
Figure 17C:
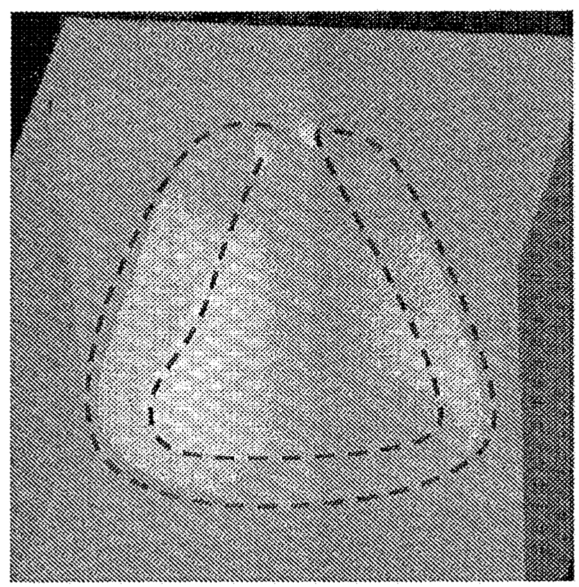

FIGS. 17A-C illustrate the same idea. FIG. 17A shows a generally conical region of excavated cancellous bone beneath a layer of compact bone, a cavity that could possibly be made with a bone harvesting device having a straight distal portion. FIG. 17B shows a larger, generally bell-shaped region of excavated cancellous bone beneath a layer of compact bone, a cavity that could be made with a bone harvesting device having a curved distal portion. FIG. 17C shows the difference between the two cavities, illustrating the additional cancellous bone available to the device with the curved distal portion.

Figures 18A, 18B, 18C:
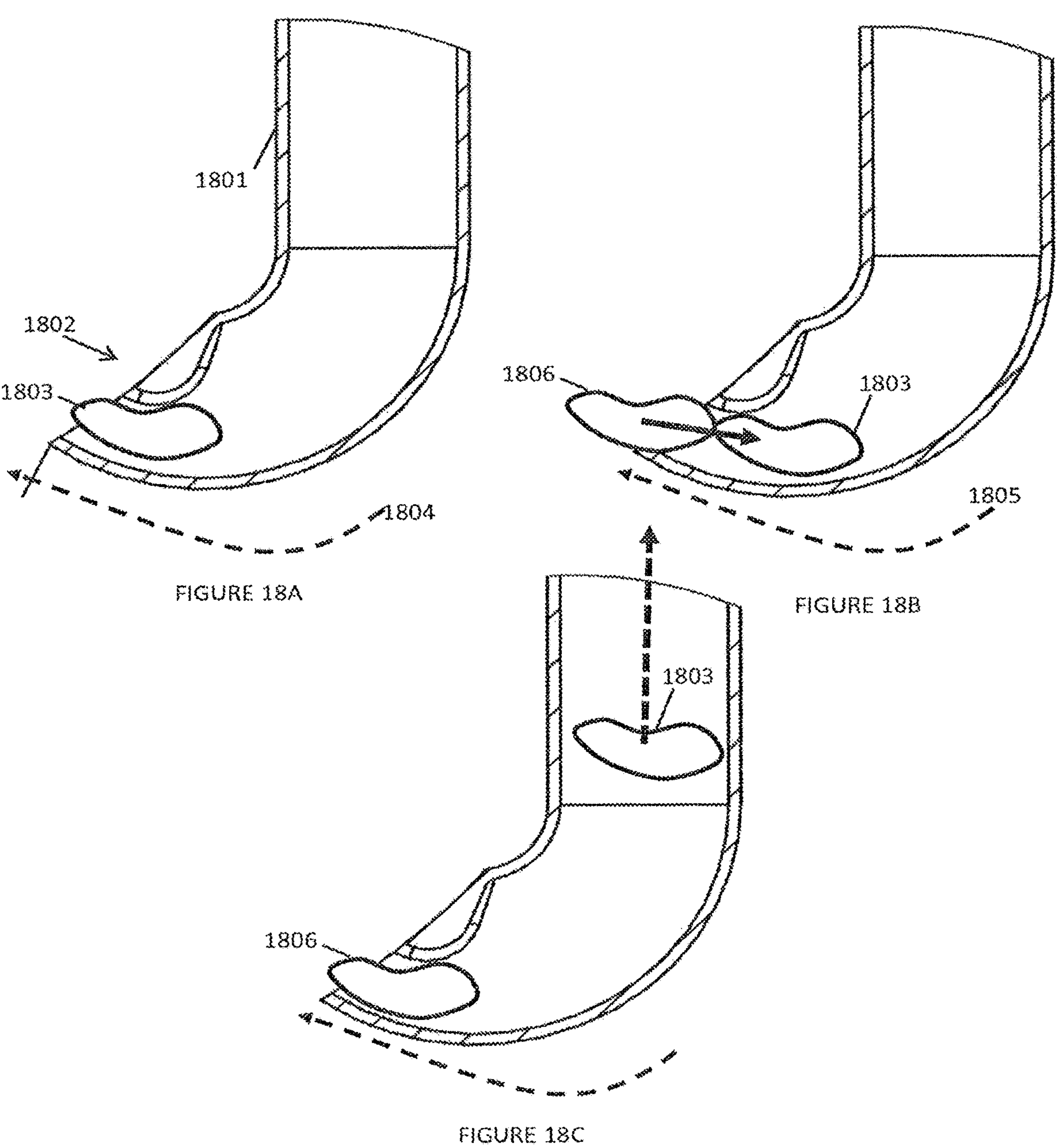
FIGS. 18A-C illustrate a benefit of having a bone harvesting device with a partially occluded tip FIGS. 19A and B schematically show a bone harvesting device with a handle flattened on one side.

FIGS. 18A-C illustrate a benefit of having a bone harvesting device 1801 with a partially occluded tip 1802. When a first portion of bone 1803 is carved and pushed into the distal end 1801 with a first cutting stroke 1804, the first portion will typically fill the distal opening, and will often be stuck in the distal opening by slight interference with the distal portion. On the second stroke 1805, a second portion of bone 1806 will be pushed into the distal end, and will displace the first portion of bone 1803, pushing the first portion farther into the harvesting device. Once the second stroke is complete and the first portion is freed, the first portion will experience a suddenly strengthened force due to the applied negative pressure in the cannula so that the first portion will be pulled up the cannula into the handle (not shown). This effect will be present whenever a subsequent portion of bone frees a previous portion of bone, but it will be exaggerated when the cannula is tapered so as to broaden toward the proximal end and the handle. This with the added concentration of pressure due to the occluding member provides a continuous collection method. One benefit of such a system is that bone can be harvested continuously without withdrawing the device from the cavity.

FIGS. 19A and B schematically show a bone harvesting device with a handle flattened on one side. The generally cylindrical or conical handle 1901 can be flattened 1902 on one side. The flattened side 1902 can be aligned 1903 with the curvature of the cutting tip so that a user who is unable to directly visualize the tip can nonetheless always be aware of its orientation. The flattened side 1902 can be clear to allow the user to see the harvested bone being collected in the handle 1901. The flattened side 1902 can also include graduations 1904 to allow a user to estimate the quantity of bone harvested. The orientation of the curvature of the cutting could alternatively be noted by colors, shading, raised or grooved or bossed or embossed tactile features.

Figures 20A, 20B:
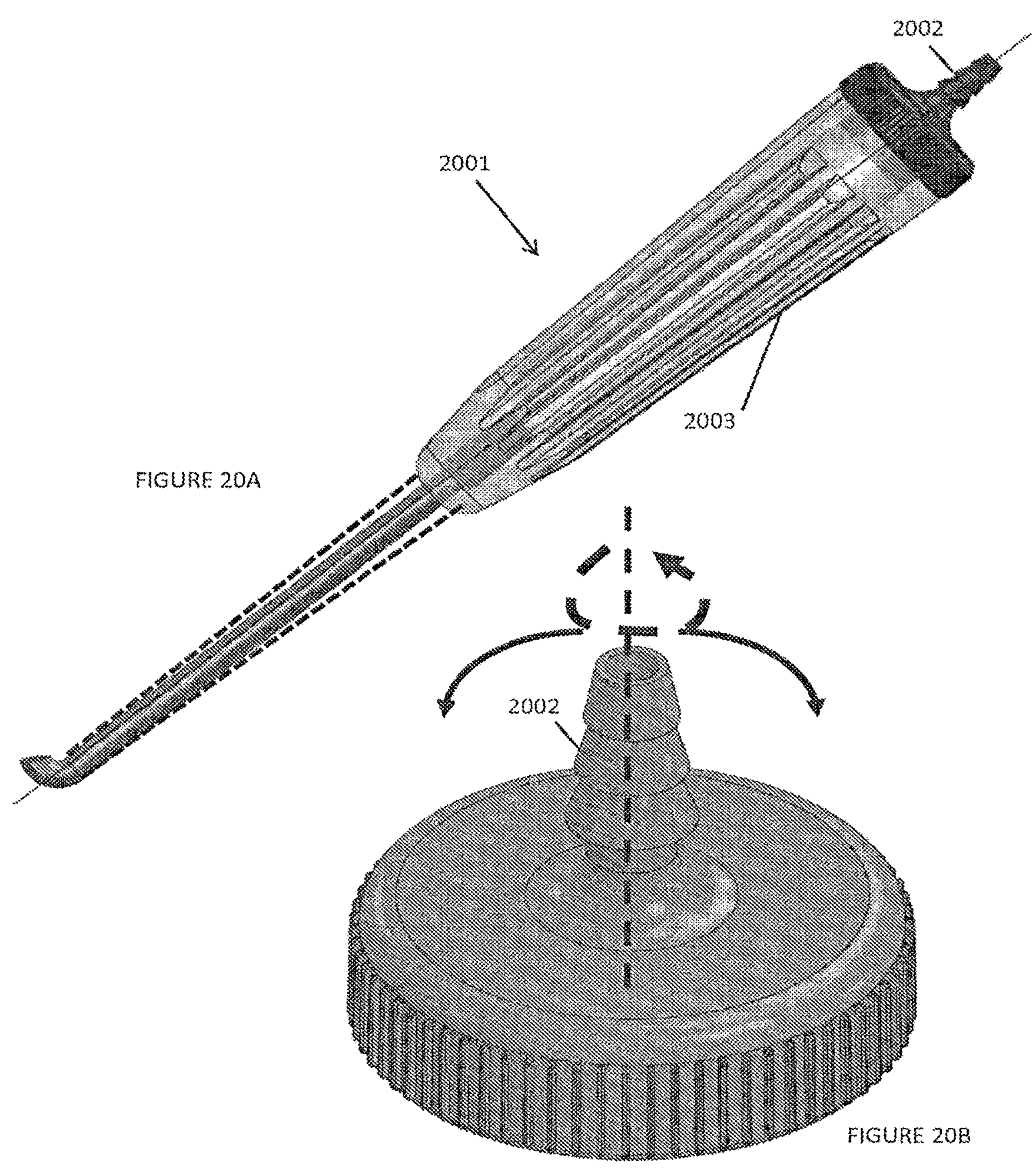
FIGS. 20A and B schematically show a bone harvesting device with a flexible or swivel suction port.

FIGS. 20A and B schematically show a bone harvesting device 2001 with a flexible or swivel suction port 2002. As shown, the port 2002 has an axis of symmetry that is generally parallel to an axis of symmetry of the handle or bone receptacle 2003. The flexibility of the port 2002 allows suction be applied even as the port is bent or twisted away from its relaxed orientation.

Figures 21A, 21B, 21C:
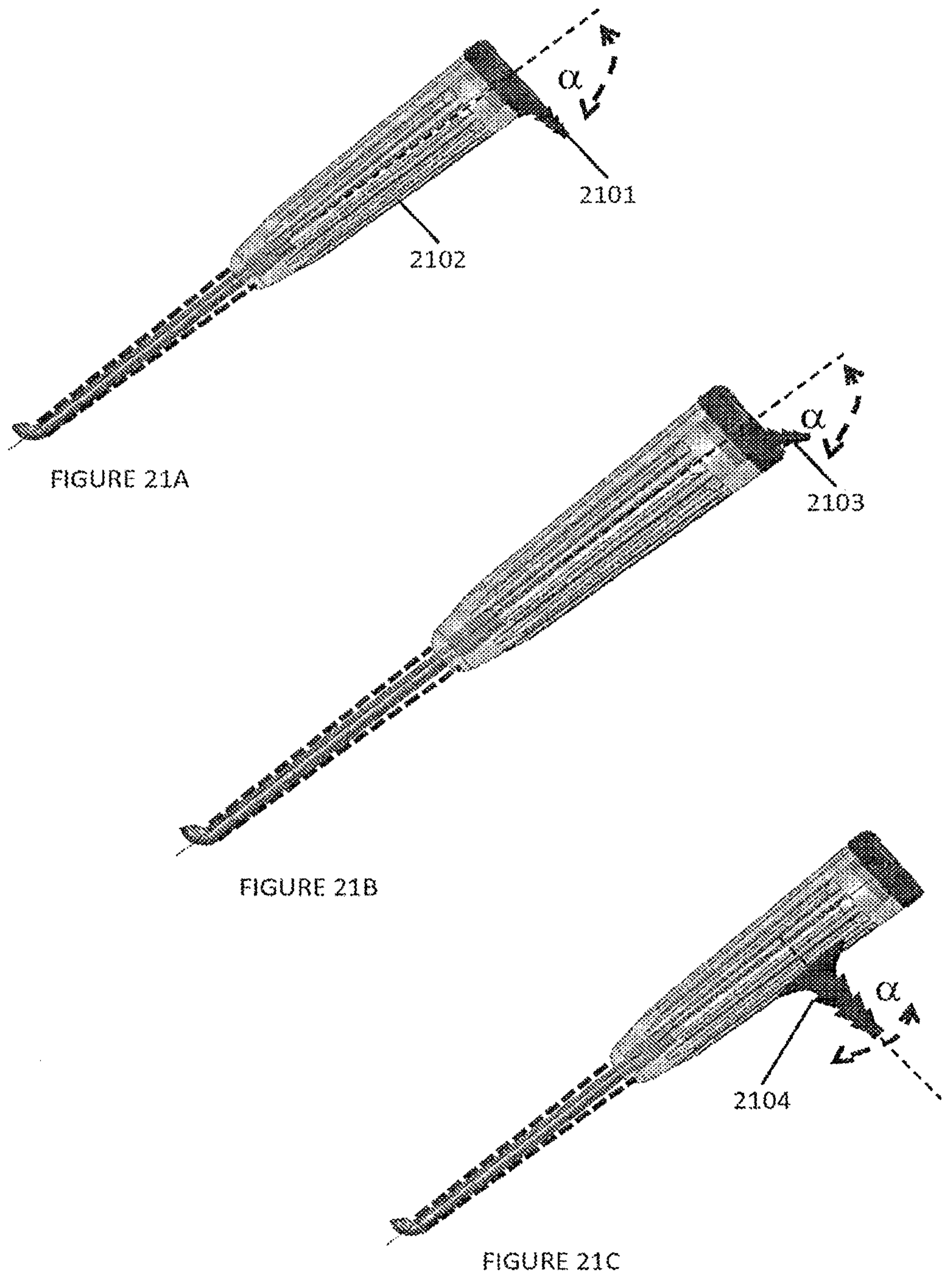
FIGS. 21A-C schematically show a bone harvesting device with various types of suction port locations and orientations.

FIGS. 21A-C schematically show a bone harvesting device with various types of suction ports. Suction port 2101 is generally perpendicular to an axis of symmetry of the bone receptacle 2102 and located at the end of the bone receptacle. Suction port 2103 is neither parallel to nor perpendicular to the axis of symmetry of the bone receptacle. Suction port 2104 is generally perpendicular to an axis of symmetry of the bone receptacle, and is located on the side-wall of the receptacle rather than at the end. This port also can be oriented with various angles from the shown location.

Figures 22A, 22B:
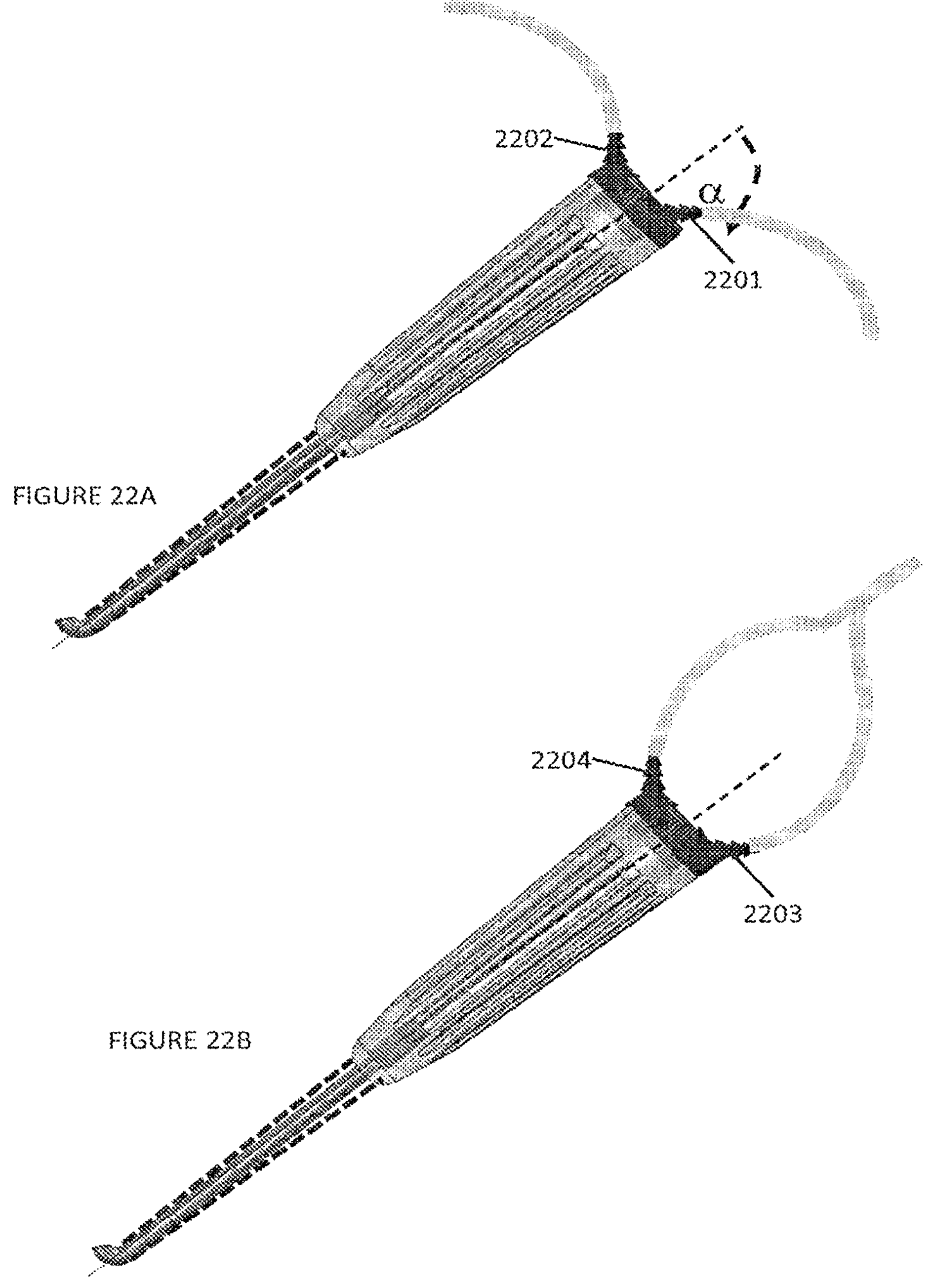
FIGS. 22A and B schematically show a bone harvesting device with multiple suction ports.

FIGS. 22A and B schematically show a bone harvesting device with multiple suction ports. FIG. 22A shows a bone harvesting device with two suction ports 2201, 2202 each connected to a different suction source. FIG. 22B shows a bone harvesting device with two suction ports 2203, 2204 each connected to the same suction source. Multiple ports could be included as a means to prevent clogging and maintain suction in the bone-harvesting device.

Figure 23:
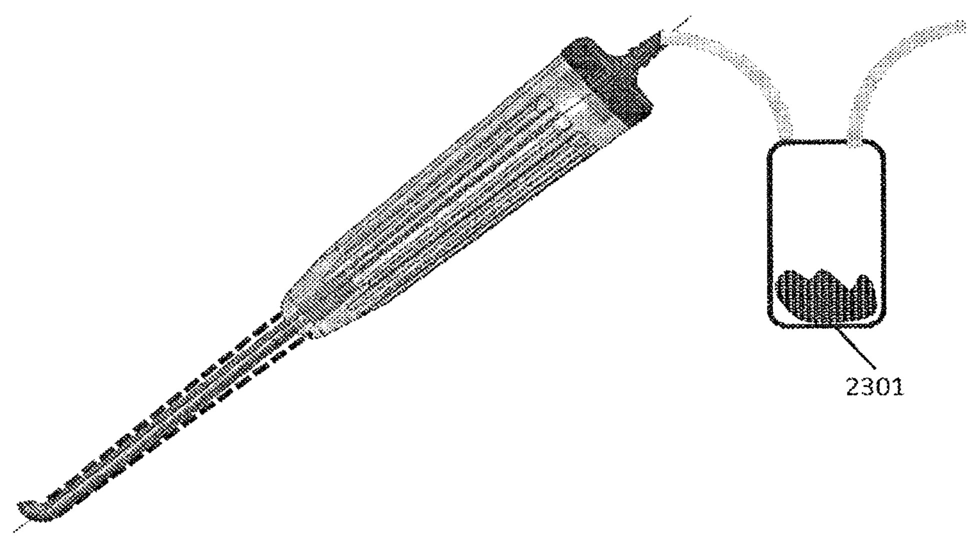
FIG. 23 schematically shows a bone harvesting device with a blood or biological material reservoir in the suction line.

FIG. 23 schematically shows a bone harvesting device with a blood or biological material reservoir 2301 in the suction line. Since, as explained above, the bone receptacle can include a filter that prevents passage of bone particles larger than a certain size, but allows passage of blood and smaller particles, it can be useful to station a blood reservoir in the fluid path of the suction line. The reservoir can be configured to allow blood and small particles to settle out of the fluid path, thus maintaining suction.

FIG. 24 schematically shows a bone harvesting device with depth markings 2401 along the cannula. Because the distal tip of the device can be hidden inside the bone when in use, external depth markings can help the user estimate how far inside the bone the distal tip has advanced.

Figure 25:
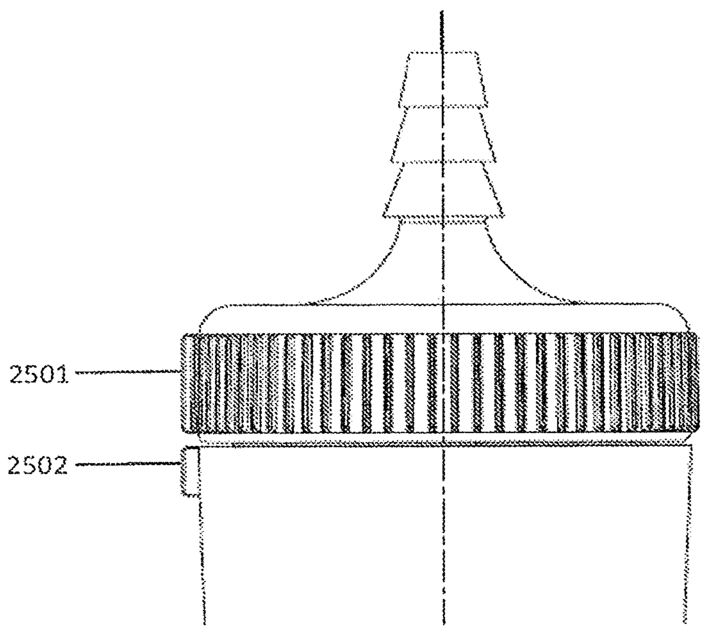
FIG. 25 schematically shows a bone receptacle and screw-on cap with alignment markers.

FIG. 25 schematically shows a bone receptacle and screw-on cap with alignment markers 2501 and 2502 to indicate to a user whether the cap has been fully secured to the bone receptacle. When the markers are aligned as shown, the user can be confident that the cap is property secured to the receptacle.

Figure 26:
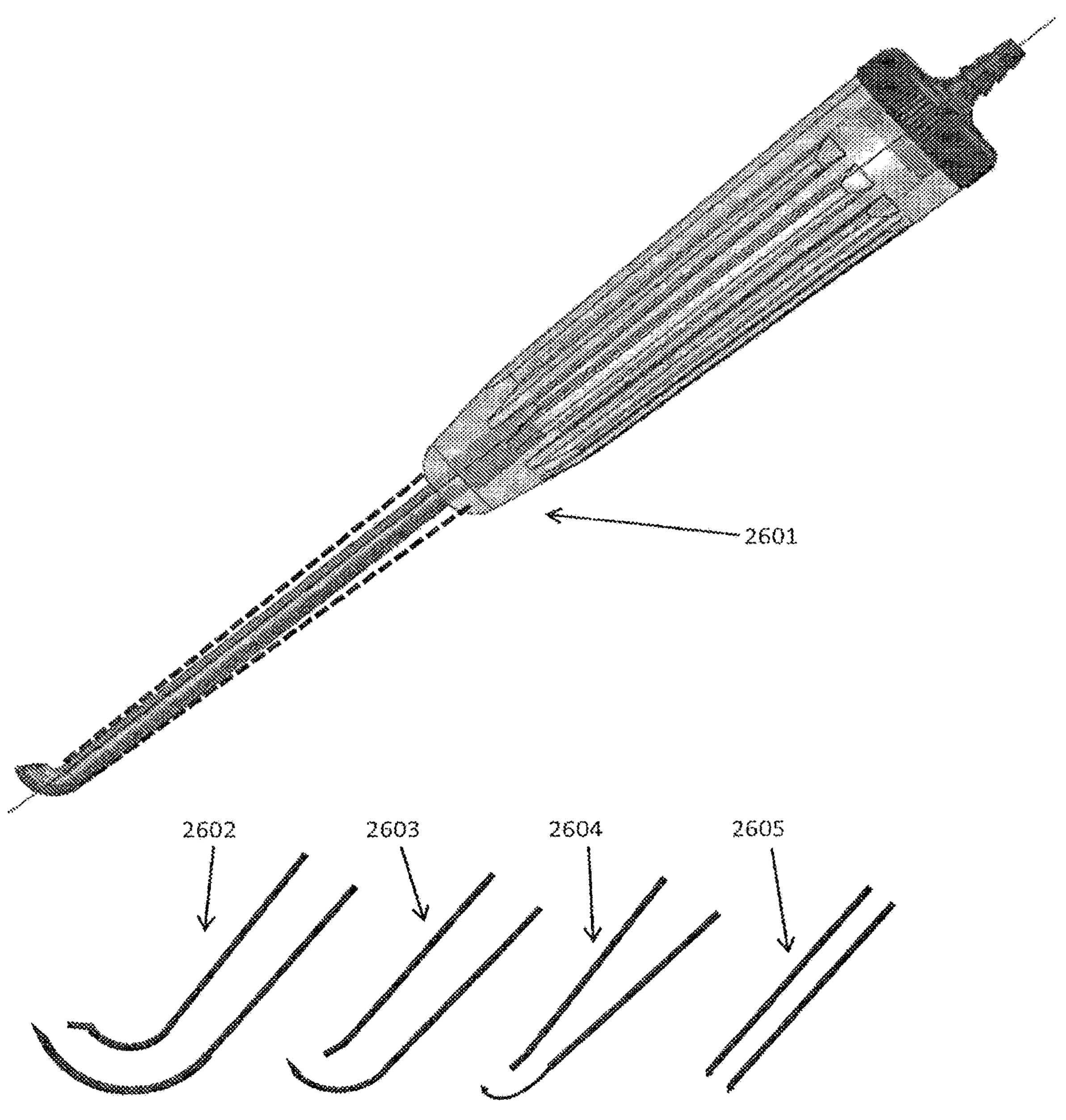
FIG. 26 shows a bone harvesting device with interchangeable distal portions.

FIG. 26 shows a bone harvesting device 2601 with interchangeable distal portions. Distal portion 2602 is similar to the distal portion shown in FIG. 2. Distal portion 2603 curves through a shorter angular arc. Distal portion 2604 is tapered, and curves through a still smaller arc. Distal portion 2605 is essentially straight and curves though no arc at all. Interchangeability allows the user to choose the best tip for any given application. 2604 will not be capable of cutting bone outside of the site of the cannula whereas 2603 is capable of cutting cancellous bone outside of the site of the cannula. This is a key feature of the bone-harvesting device enabling it to reach in areas where current bone-harvesting devices cannot.

Figure 27:
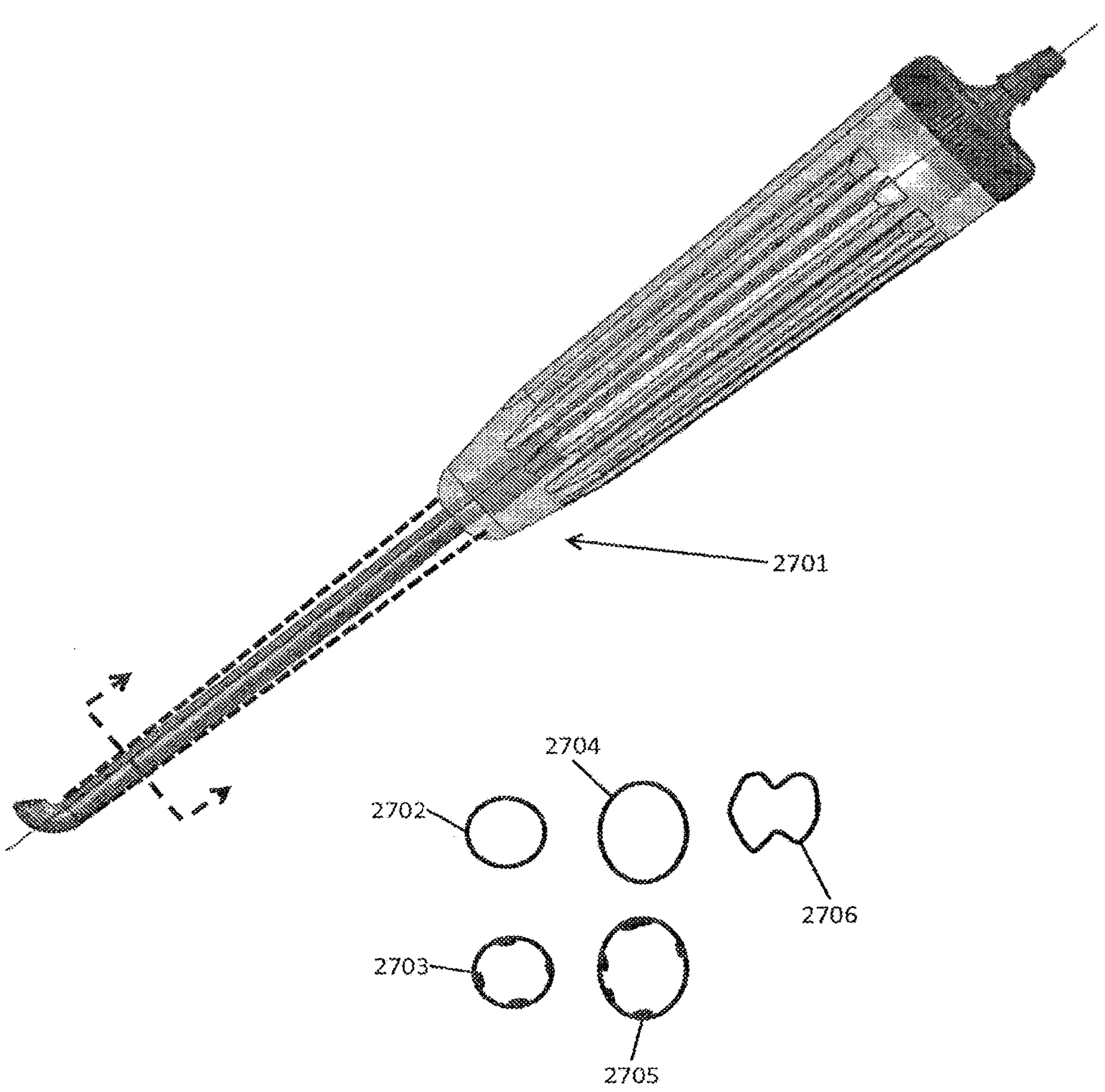
FIG. 27 schematically shows a bone harvesting device with a cannula having various different cross-sectional geometries.

FIG. 27 schematically shows a bone harvesting device 2701 with a cannula having various different cross-sectional geometries. The cross-section as shown could be, for example, circular 2702, elliptical 2704, or irregular 2706, or any other useful two dimensional shape. The cannula might have ribs on the interior as shown in 2703 and 2705. The various profiles could allow for irrigation to flow through the raised regions and/or other means of positive pressure to aid in clearing the cannulated portion. The profiles may also be apparent from various manufacturing processes and by enabling such geometries it can aid in the manufacturing processes.

Figure 28:
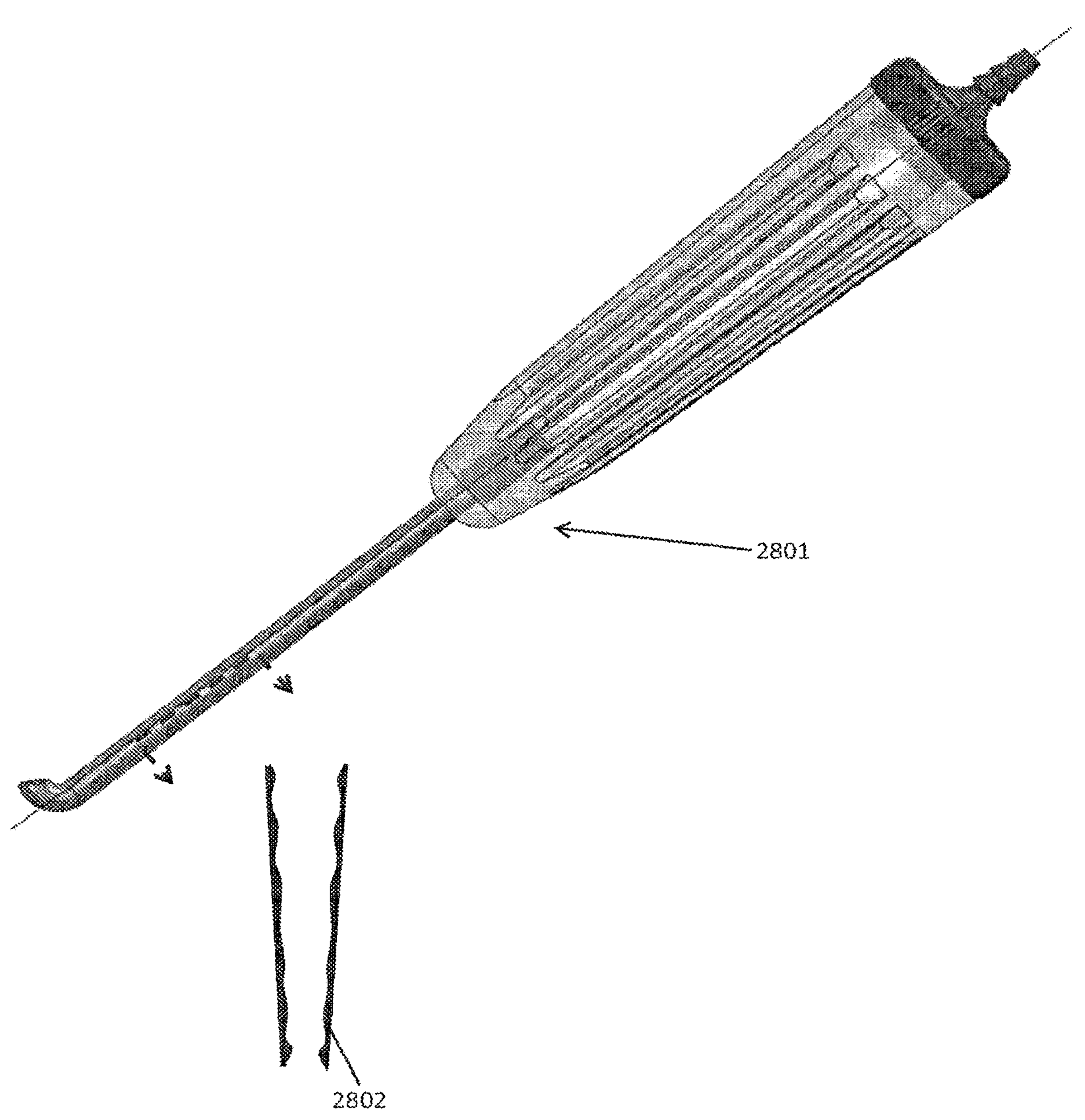
FIG. 28 schematically shows a bone harvesting device with a cannula having a wall thickness that varies along its length.

FIG. 28 schematically shows a bone harvesting device 2801 with a cannula having a wall thickness that varies along its length. Depending on manufacturing process, variable thickness may aid in ease of manufacturing. In addition, the grooves could have irrigation and/or positive pressure to aid in streamlined suction.

Figure 29:
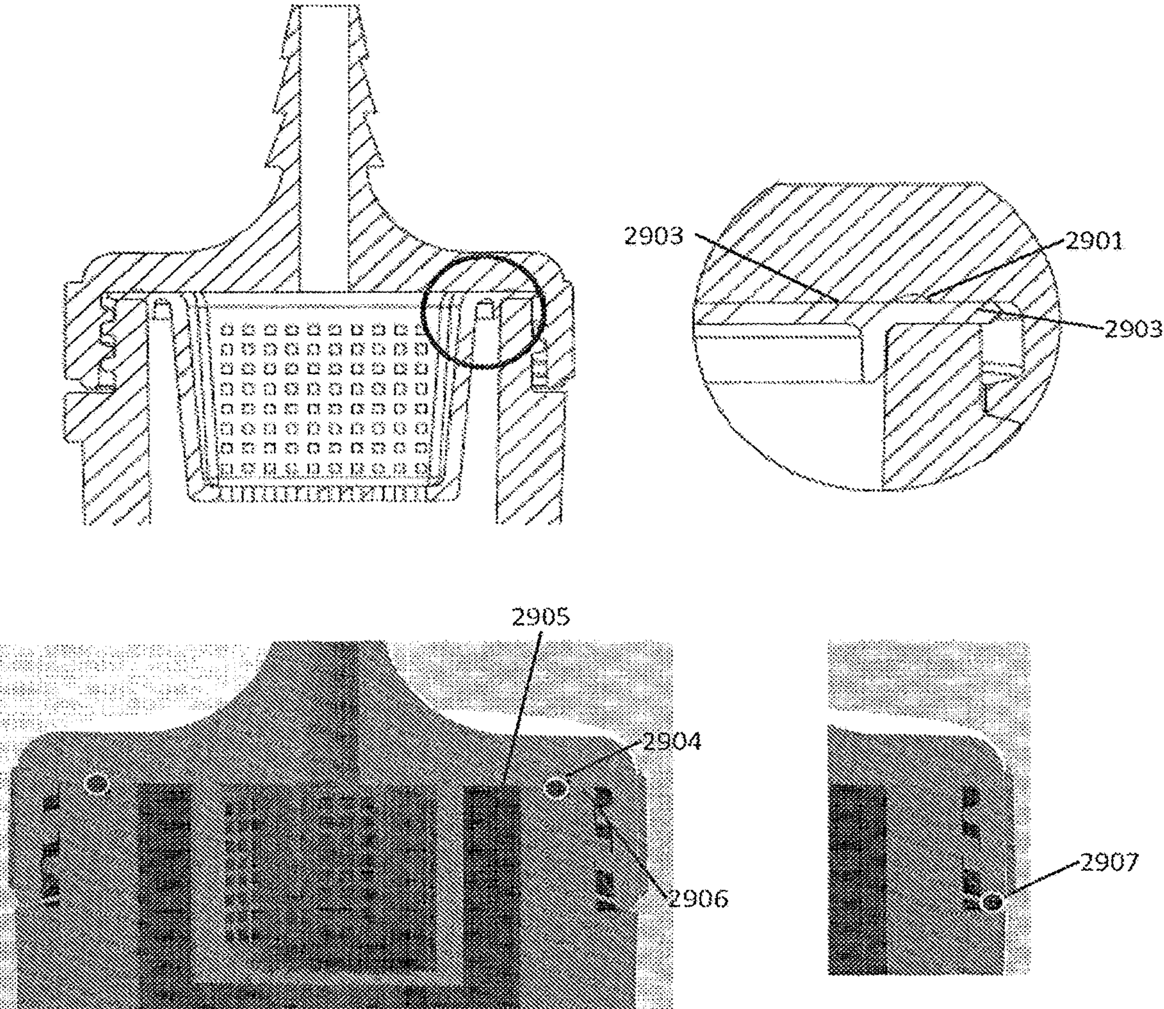
FIG. 29 schematically shows a cap for a bone receptacle with various sealing points.

FIG. 29 schematically shows a cap for a bone receptacle with various sealing points. In one embodiment, a seal 2901 is positioned in the lower surface of the cap 2902, facing the upper surface of a separate filter assembly 2903. In another embodiment, the seal 2904 is positioned between the lower surface of a cap 2905, which includes an integral filter assembly, and the upper surface of the receptacle 2906. In that case the seal is inside the screw threads that affix the cap to the receptacle. In another embodiment, the seal 2907 is outside the screw threads that affix the cap to the receptacle.

Figure 30:
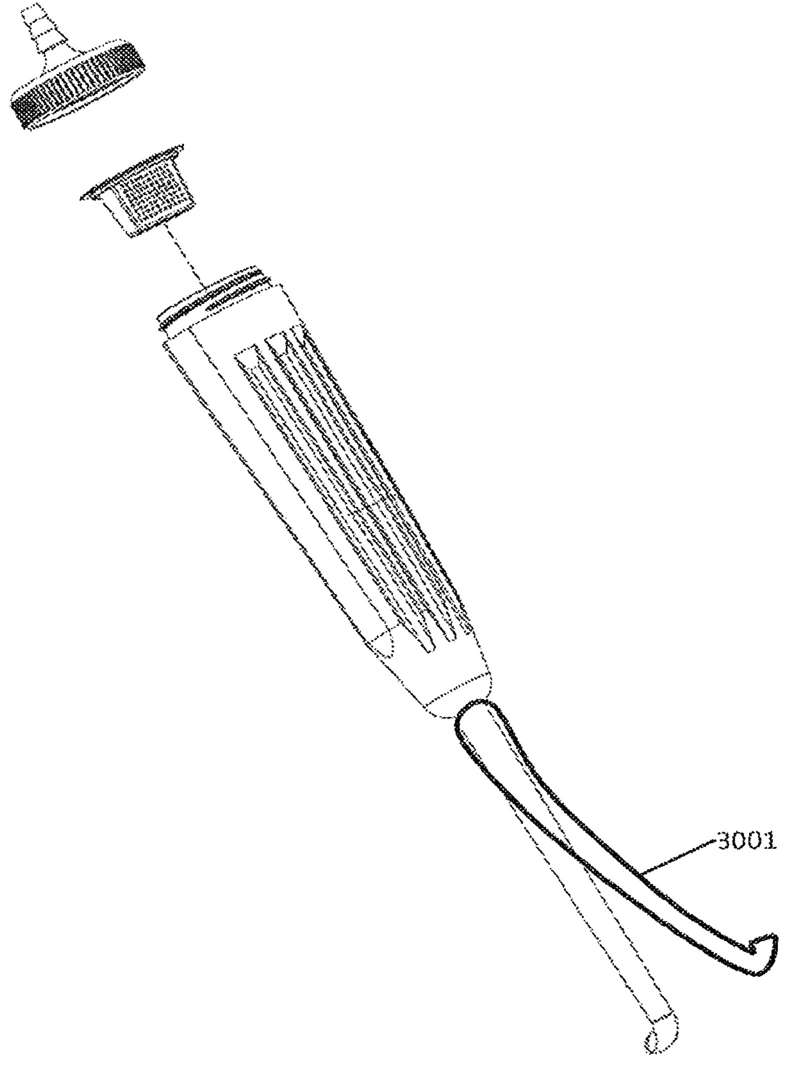
FIG. 30 schematically shows a bone harvesting device in which the cannula portion may be curved.

FIG. 30 schematically shows a bone harvesting device in which the cannula 3001 portion may be curved. A curved cannula may improve the reach of the device and may offer a cutting reach greater than if it is only straight.

Figure 31:
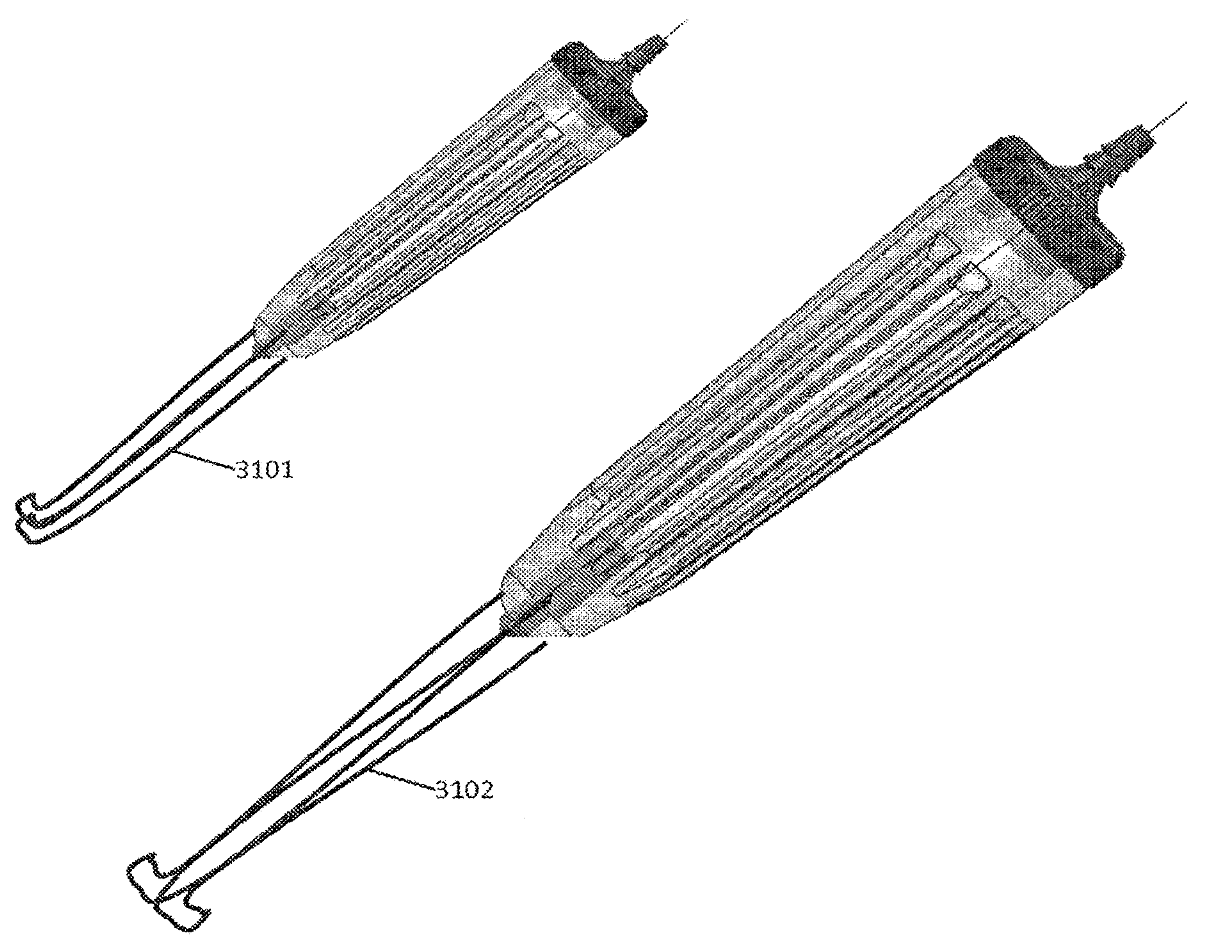
FIG. 31 schematically shows a bone harvesting devices including two cannulas in various orientations.

FIG. 31 schematically shows a bone harvesting devices including two cannulas. A device with two cannulas can either include cannulas with cutting portions in parallel 3101, or cutting portions in facing opposite directions or angled in different directions either radially, laterally or longitudinally. 3102.

Figures 32A, 32B, 32C:
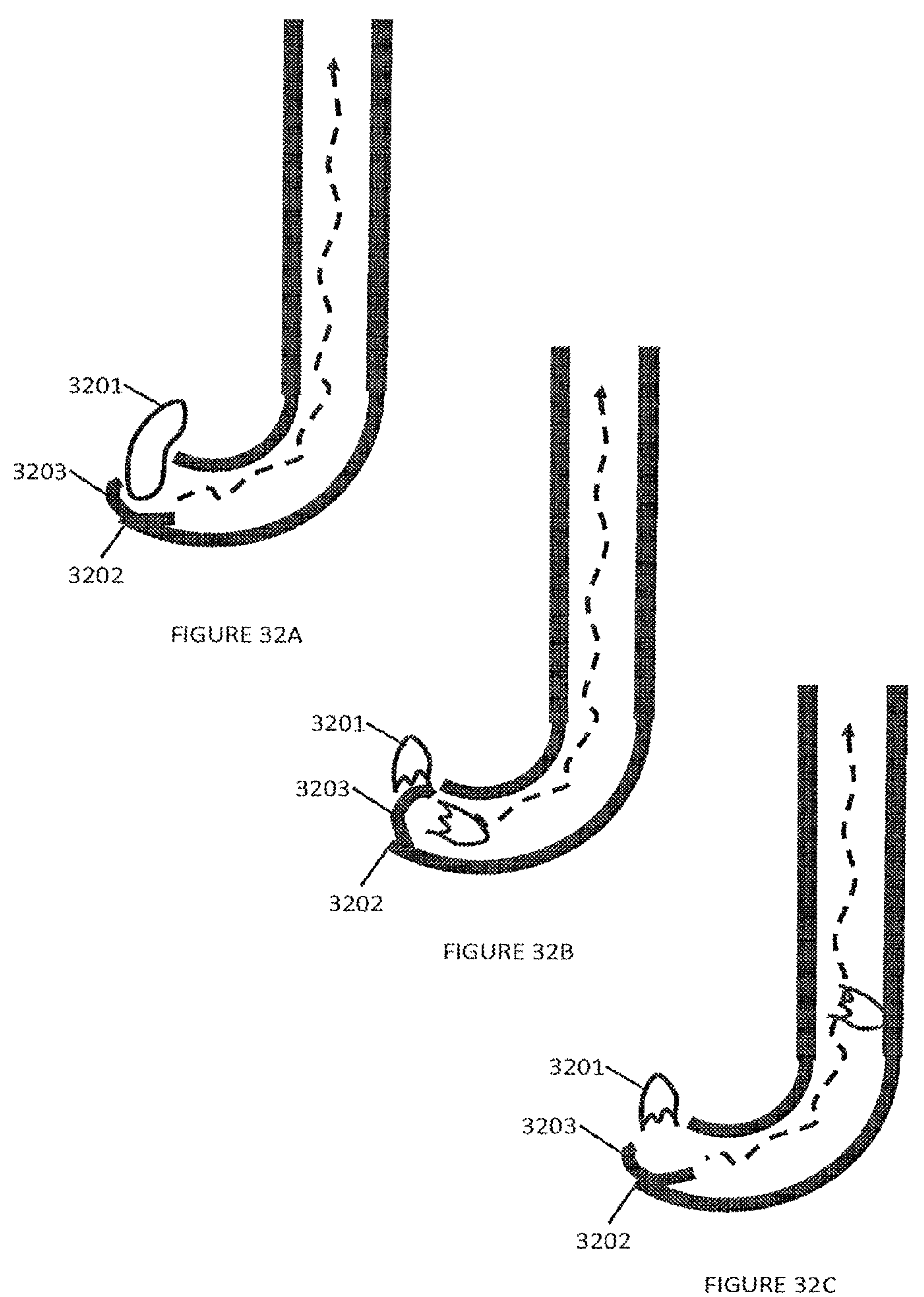
FIGS. 32A-C schematically show an actuated distal tip.

FIGS. 32A-C schematically show an actuated distal tip. This embodiment provides an automated cutting action where the user advanced the distal tip into a boney region and cancellous bone and 3201 is scraped into the distal tip 3202, the cutting surface 3203 or a portion thereof can be actuated so as to close against the opposite side of the distal tip. This will actively cut any bone occupying the opening of the distal tip. The actuated cutting surface can be a spinning blade. The actuation can be magnetic, electromechanical, purely mechanical (i.e. as by wire), or by any other useful mode. The effect is to bite off bone fragments rather than simply to scrape or cut manually with the distal tip.

FIGS. 33A-C schematically show different sharpened distal tips. Tip 3301 is sharpened on the inside of the cannula. Tip 3302 is sharpened on the outside of the cannula. Tip 3303 is sharpened on both the inside and the outside of the cannula. The tip can also be sharpened in one or more portions and not in one or more other portions, for example to create a serrated edge or other configuration.

The distal cutting tip can be coupled with irrigation.

All versions of the device described above can be part of a kit that, for example, could include combinations of the following: a flexible plunger, a stiff plunger, elongated accessory to remove material from bone receptacle, a hole saw, trephine device, drill tap, guidewire, reamer/drill bit, cannulated reamer/drill bit, or reamer/drill bit sleeve for penetrating the compact bone, interchangeable cutting tips, and/or separate biological material catching unit such as a blood reservoir.

Any of the devices and methods disclosed herein can also include technology to allow the user to sense how the distal tip is interacting with the bone, even when the tip cannot be directly visualized. For example the tip could be visualized by use of an infrared or visible light camera, possibly an endoscopic camera, by ultrasound visualization, by piezoelectric sensors, or pressure or force sensors.

A bone-harvesting device can include a cannula and a bone receptacle. The cannula can include a proximal end, a proximal portion adjacent to the proximal end that defines an axis, a curved distal portion that bends through an angle of at least 90 degrees and no more than 180 degrees relative to the axis, and a distal end, adjacent to the distal portion, at least a part of the distal end being sharpened to form a cutting edge. The bone receptacle can include a suction port and an entry port. The entry port can be attached to the proximal end of the cannula such that, when suction is applied to the suction port, the suction draws from the distal end of the cannula, through the cannula, and into the bone receptacle. In such bone-harvesting devices, the cannula can further include an occluding member that partially, but not fully, occludes the distal end. At least a portion of the proximal portion can be curved and not lie along the axis. The cross-sectional geometry of the proximal portion can vary along the length of the proximal portion. The cross-sectional geometry of the proximal portion can be constant along the length of the proximal portion. The suction port can be constructed of a flexible material so that suction may be continuously applied to the suction port while port is bent into different orientations relative to the rest of the device. An axis of symmetry in the suction port can be either parallel or non-parallel to an axis of symmetry in the bone receptacle. The receptacle can include a plurality of suction ports. The receptacle can define a proximal opening and can include a cap removably attached to the bone receptacle thereby sealing the opening. The cap can be removably attached with any one of (a) mating screw threads, (b) an interference fit, (c) a latch, or (d) a clip. The exterior of the bone receptacle is configured to be used as a handle by a human operator. The suction port can be in fluid communication with a reservoir configured to allow passage of gases but to trap liquids and solids.

A bone-harvesting device can include a cannula and a bone receptacle. The cannula can includes a proximal end, a straight proximal portion, a curved distal portion, and a distal end, adjacent to the distal portion, at least a part of the distal end being sharpened to form a cutting edge. The bone receptacle can include a suction port, an entry port, and a filter that (a) fully covers the suction port, and (b) includes at least two sieves positioned so as to have different orientations relative tt the suction port. In such devices each sieve can be generally planar with no two sieves being parallel. The entry port can be attached to the proximal end of the hollow cannula such that, when suction is applied to the suction port, the suction draws from the distal end of the cannula, through the cannula, and into the bone receptacle.

A method of harvesting cancellous bone can include selecting a bone in a patient from which cancellous bone will be harvested, the bone including cancellous bone and compact bone, exposing the cancellous bone by creating a pilot hole through the compact bone, advancing a distal end of a bone harvesting device into the pilot hole along an axis of the bone harvesting device, the distal end including a cutting edge, and excavating cancellous bone into the bone harvesting device by applying the cutting edge to the cancellous bone in a direction not parallel to the axis of the bone harvesting device. The method can include collecting the excavated cancellous bone by drawing the excavated bone through a channel defined by the bone harvesting device without removing the distal end of the bone harvesting device through the pilot hole. In such methods, excavating cancellous bone can include excavating cancellous bone that is not visible along any line of sight through the pilot hole.

We claim:

1. A bone harvesting device, comprising:

a hollow cannula;

a bone receptacle coupled to a proximal end of the hollow cannula, the bone receptacle including an opening in a proximal end thereof that opens to an interior of the bone receptacle, wherein, in use of the bone harvesting device, applying a suction force to the interior of the bone receptacle can draw harvested bone into the interior through the hollow cannula;

a removable plunger removably received in the interior of the bone receptacle, the removable plunger including a distal plate, a proximal plate, and a first longitudinally-extending wall section that extends between the distal plate and the proximal plate to establish a bone containment region in the removable plunger for collecting bone between the distal plate and the proximal plate, the bone containment region including a closed first side that is provided by the first longitudinally-extending wall section and an open second side that allows for removal of harvested bone from the bone containment region, the removable plunger further including a second longitudinally-extending wall section that extends in a proximal direction away from the proximal plate outside the bone containment region; and a cap removably secured to the bone receptacle over the opening in the proximal end of the bone receptacle, wherein the removable plunger is positionable entirely within the bone receptacle when the cap is secured to the bone receptacle.

2. The bone harvesting device of claim 1, wherein the hollow cannula includes an interior passage therein that passes through a proximal end region and a distal end region of the hollow cannula, wherein the proximal end region extends along a longitudinal axis such that the interior passage, in passing through the proximal end region, extends along said longitudinal axis, and wherein the distal end region curves away from the longitudinal axis through an arc whose angular extent is greater than 90 degrees relative to the longitudinal axis such that the interior passage, in passing through the distal end region, extends along said arc.

3. The bone harvesting device of claim 2, wherein the angular extent is no more than 180 degrees relative to the longitudinal axis.

4. The bone harvesting device of claim 2, wherein the angular extent is between 120-150 degrees relative to the longitudinal axis.

5. The bone harvesting device of claim 2, wherein the distal end region includes an opening in an exterior thereof that opens to the interior passage.

6. The bone harvesting device of claim 5, wherein the distal end region includes an occluding geometry that partially occludes the interior passage at the opening.

7. The bone harvesting device of claim 6, wherein the occluding geometry comprises an occluding plate.

8. The bone harvesting device of claim 7, wherein the occluding plate extends across a portion of the interior passage at the opening.

9. The bone harvesting device of claim 5, wherein the distal end region includes a cutting surface proximate the opening.

10. The bone harvesting device of claim 9, wherein the cutting surface defines an edge of the opening.

11. The bone harvesting device of claim 5, wherein the opening is located at a terminal end of the interior passage.

12. The bone harvesting device of claim 2, wherein the proximal end region of the hollow cannula tapers longitudinally such that a distal-most part of the proximal end region has a smaller cross-sectional area than a proximal-most part of the proximal end region.

13. The bone harvesting device of claim 2, wherein the interior passage has a variable cross-sectional geometry along a length of the interior passage.

14. The bone harvesting device of claim 2, wherein the bone receptacle includes a flattened handle portion that is directionally aligned with the way the distal end region curves away from the longitudinal axis.

15. The bone harvesting device of claim 1, wherein the hollow cannula includes: (i) a distal opening in an exterior thereof that opens to an interior passage in the hollow cannula which passes through the hollow cannula; and (ii) an occluding geometry that partially occludes the interior passage at the distal opening.

16. The bone harvesting device of claim 1 further comprising a suction port in communication with the bone receptacle.

17. The bone harvesting device of claim 16, wherein the suction port is formed on the removable cap.

18. The bone harvesting device of claim 1 further comprising a filter positionable inside the bone receptacle for blocking parts of the harvested bone from passing through the suction port.

19. The bone harvesting device of claim 18, wherein the filter includes multiple separate sieve sections that are separated from one another along an exterior of the filter.

20. The bone harvesting device of claim 1, wherein the distal plate and the proximal plate each include respective openings therein to allow harvested bone to pass through the distal plate and the proximal plate.

* * * * *